United States Patent
Auld et al.

(10) Patent No.: US 10,182,906 B2
(45) Date of Patent: Jan. 22, 2019

(54) INTRAOCULAR LENS INSERTER WITH TEMPERATURE COMPENSATION

(71) Applicant: ALCON PHARMACEUTICALS LTD., Fribourg (CH)

(72) Inventors: Jack R. Auld, Laguna Niguel, CA (US); John C. Huculak, Mission Viejo, CA (US); Matthew McCawley, San Clemente, CA (US); Matthew Flowers, Aliso Viejo, CA (US)

(73) Assignee: Alcon Pharmaceuticals, Ltd., Fribourg (CH)

( * ) Notice: Subject to any disclaimer, the term of this patent is extended or adjusted under 35 U.S.C. 154(b) by 548 days.

(21) Appl. No.: 14/800,687

(22) Filed: Jul. 15, 2015

(65) Prior Publication Data
US 2016/0015511 A1 Jan. 21, 2016

Related U.S. Application Data

(60) Provisional application No. 62/024,886, filed on Jul. 15, 2014.

(51) Int. Cl.
*A61F 2/16* (2006.01)

(52) U.S. Cl.
CPC ............ *A61F 2/167* (2013.01); *A61F 2/1662* (2013.01)

(58) Field of Classification Search
CPC ...... A61F 2/167; A61F 2/1662; A61F 2/1664; A61F 2/1667; A61F 2/1675; A61F 2/1678
See application file for complete search history.

(56) References Cited

U.S. PATENT DOCUMENTS

| | | | |
|---|---|---|---|
| 8,225,643 B2 | 7/2012 | Abboud et al. |
| 8,968,396 B2 | 3/2015 | Matthews et al. |
| 9,255,665 B2 | 2/2016 | Brouillette et al. |
| 2008/0004610 A1 | 1/2008 | Miller et al. |

(Continued)

FOREIGN PATENT DOCUMENTS

| | | |
|---|---|---|
| CA | 2858485 | 6/2013 |
| EP | 1144031 B1 | 10/2005 |

(Continued)

OTHER PUBLICATIONS

International Search Report for International Application No. PCT/US2015/040667, Publication No. WO2016/011215, dated Nov. 11, 2015, 4 pages.

(Continued)

*Primary Examiner* — Todd Scherbel
*Assistant Examiner* — Brooke Labranche

(57) ABSTRACT

An intraocular lens inserter can include an energy storage portion, an actuator portion that provides temperature compensation, and a lens support portion. The energy storage portion can include a compressible energy storage device, such as a compressible fluid, springs, and other devices. The inserter can include an actuator portion operating with a substantially incompressible fluid. The actuator can be configured to provide an operator with control over the release of pressurized fluid so as to move a plunger for the discharge of a lens from an intraocular lens cartridge, discharge of the lens being limited based at least in part on pressure feedback from the pressurized fluid due temperature increases.

14 Claims, 16 Drawing Sheets

(56) References Cited

U.S. PATENT DOCUMENTS

| | | | |
|---|---|---|---|
| 2009/0018548 A1* | 1/2009 | Charles | A61F 2/1662 |
| | | | 606/107 |
| 2009/0292293 A1 | 11/2009 | Bogaert et al. | |
| 2011/0264102 A1 | 10/2011 | Cole et al. | |
| 2011/0264103 A1 | 10/2011 | Cole et al. | |
| 2012/0296264 A1 | 11/2012 | Boukhny et al. | |
| 2014/0276898 A1* | 9/2014 | Novak | A61F 2/167 |
| | | | 606/107 |
| 2015/0088149 A1 | 3/2015 | Auld | |
| 2015/0154049 A1 | 6/2015 | Xu et al. | |

FOREIGN PATENT DOCUMENTS

| | | |
|---|---|---|
| EP | 1865885 | 4/2010 |
| EP | 1539065 | 12/2012 |
| EP | 1748811 | 12/2012 |
| EP | 2178464 | 8/2013 |
| EP | 2560578 | 6/2016 |
| EP | 3122286 | 2/2017 |
| JP | 4138428 A2 | 5/1992 |
| WO | 2013086612 | 6/2013 |
| WO | 2013184727 A1 | 12/2013 |
| WO | 2013184727 | 2/2014 |
| WO | 2014089250 | 6/2014 |
| WO | 2014149459 | 9/2014 |
| WO | 2015144870 | 10/2015 |
| WO | 2015144890 A1 | 10/2015 |
| WO | 2016208725 A1 | 12/2016 |

OTHER PUBLICATIONS

Written Opinion of the International Searching Authority, International Application No. PCT/US2015/040667, Publication No. WO2016/011215, dated Nov. 11, 2015, 8 pages.

\* cited by examiner

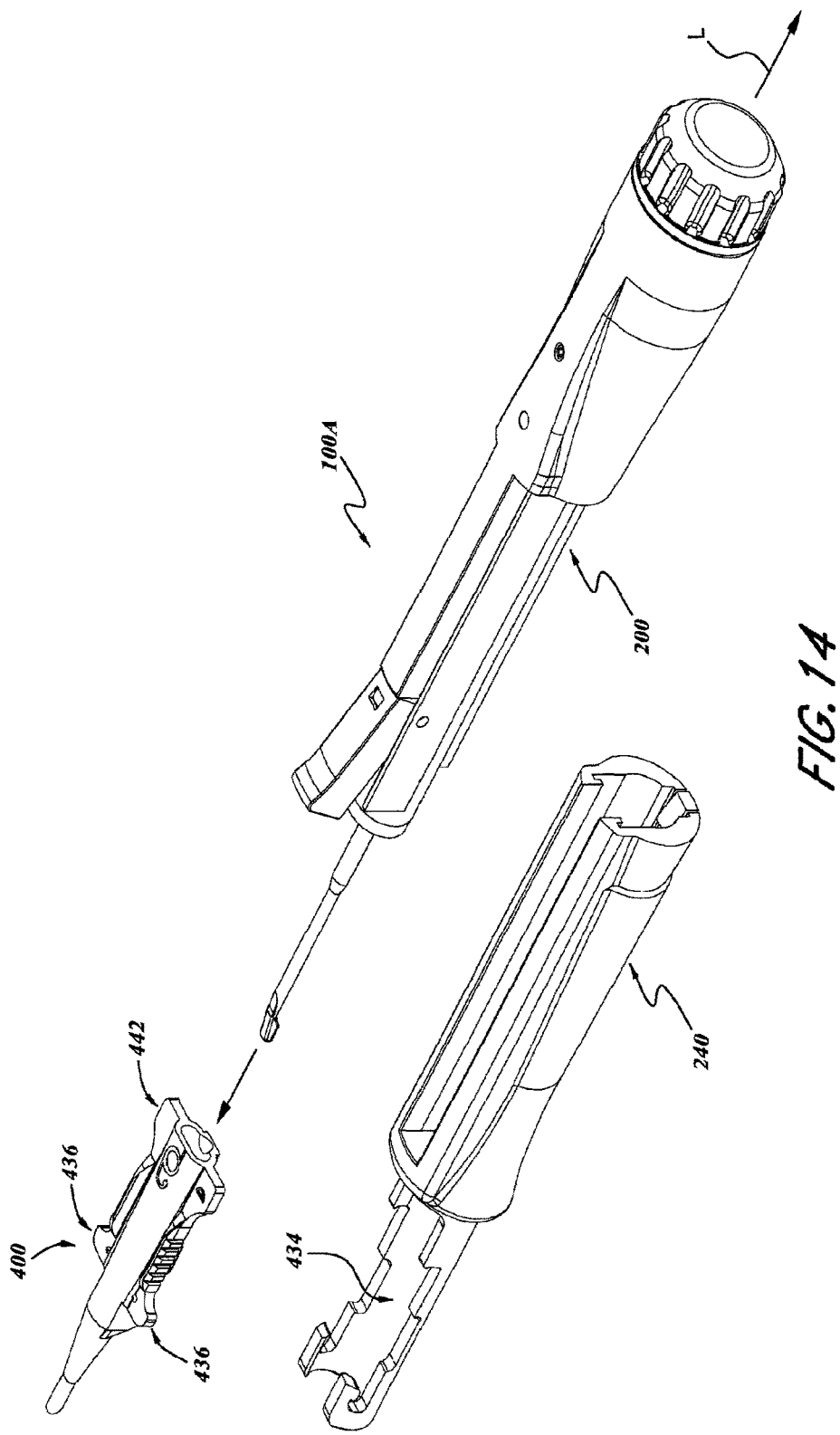

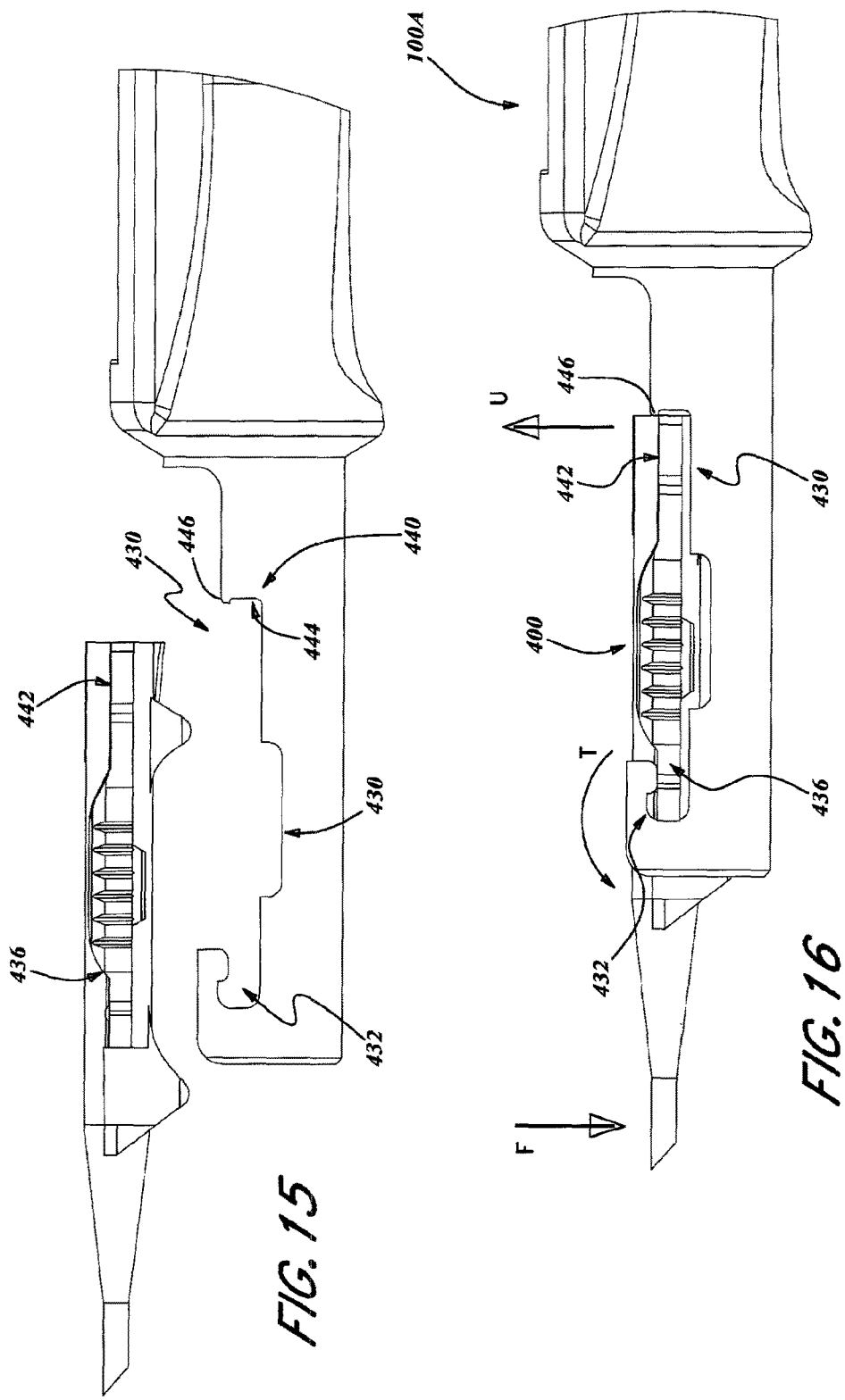

INTRAOCULAR LENS INSERTER WITH TEMPERATURE COMPENSATION

RELATED APPLICATION DATA

The present application claims the benefit of U.S. Provisional Application No. 62/024,886, filed Jul. 15, 2014, the entire disclosure of which is expressly incorporated herein by reference.

TECHNICAL FIELD

The inventions disclosed herein generally relate to devices and methods for inserting intraocular lens into an eye of an animal and, more particularly for devices and methods that provide temperature compensation to lens inserters.

BACKGROUND

A cataract is a clouding that develops in the crystalline lens of the eye or in its envelope (lens capsule), varying in degree from slight to complete opacity and obstructing the passage of light. Early in the development of age-related cataract, the power of the lens may be increased, causing near-sightedness (myopia), and the gradual yellowing and opacification of the lens may reduce the perception of blue colors. Cataracts typically progress slowly to cause vision loss, and are potentially blinding if untreated. The condition usually affects both eyes, but almost always one eye is affected earlier than the other. The following is a list of different types of cataracts:

Senile cataract—Characterized by an initial opacity in the lens, subsequent swelling of the lens, and final shrinkage with complete loss of transparency occurring in the elderly.

Morgagnian cataract—Liquefied cataract cortex forming a milky white fluid, which can cause severe inflammation if the lens capsule ruptures and leaks, occurring as a progression of the cataract. Untreated, the advanced cataract can cause phacomorphic glaucoma. Very advanced cataracts with weak zonules are liable to dislocation anteriorly or posteriorly.

Cataract resulting from trauma—A cataract resulting from trauma to the eye in an otherwise healthy individual. Blunt trauma or penetrating trauma resulting from accidental injury to the eye can result in crystalline lens opacification. Retinal surgery involving a para plana vitrectomy will result in a post-operative cataract in six to nine months after the surgery. Infrequently, an adverse event can occur where by the otherwise healthy crystalline lens is touched by a surgical instrument during retinal surgery. The crystalline lens clouds and a cataract forms within minutes of the contact.

Congenital cataract—A cataract developed in a child before or just after birth.

In the United States, age-related lenticular changes have been reported in 42% of those between the ages of 52 and 64, 60% of those between the ages 65 and 74, and 91% of those between the ages of 75 and 85.

Age-related cataract is responsible for 48% of world blindness, which represents about 18 million people, according to the World Health Organization. Continued population growth with the shift of the average age will result in increased numbers of patients with cataracts. The increase in ultraviolet radiation resulting from depletion of the ozone layer is expected to further increase the incidence of cataracts.

In many countries, surgical services are inadequate, and cataracts remain the leading cause of blindness. Cataracts are a large cause of low vision in both developed and developing countries. Even where surgical services are available, low vision associated with cataracts can remain prevalent, as a result of long waits for operations and barriers to surgical uptake, such as cost, lack of information and patient transportation problems.

Several factors can promote the formation of cataracts, including long-term exposure to ultraviolet light, exposure to ionizing radiation, secondary effects of diseases such as diabetes, hypertension and advanced age, or trauma (possibly much earlier); they are usually a result of denaturation of lens protein. Genetic factors are often a cause of congenital cataracts, and positive family history may also play a role in predisposing someone to cataracts at an earlier age, a phenomenon of "anticipation" in presenile cataracts. Cataracts may also be produced by eye injury or physical trauma.

A study among Icelandair pilots showed commercial airline pilots are three times more likely to develop cataracts than people with nonflying jobs. This is thought to be caused by excessive exposure at high altitudes to radiation coming from outer space, which becomes attenuated by atmospheric absorption at ground level. Supporting this theory is the report that 33 of the 36 Apollo astronauts involved in the nine Apollo missions to leave Earth orbit have developed early stage cataracts that have been shown to be caused by exposure to cosmic rays during their trips. At least 39 former astronauts have developed cataracts, of whom 36 were involved in high-radiation missions such as the Apollo missions.

Cataracts are also unusually common in persons exposed to infrared radiation, such as glassblowers, who suffer from exfoliation syndrome. Exposure to microwave radiation can cause cataracts. Atopic or allergic conditions are also known to quicken the progression of cataracts, especially in children. Cataracts can also be caused by iodine deficiency. Cataracts may be partial or complete, stationary or progressive, or hard or soft. Some drugs can induce cataract development, such as corticosteroids and the antipsychotic drug quetiapine (sold as Seroquel, Ketipinor, or Quepin).

The operation to remove cataracts can be performed at any stage of their development. There is no longer a reason to wait until a cataract is "ripe" before removing it. However, since all surgery involve some level of risk, it is usually worth waiting until there is some change in vision before removing the cataract.

The most effective and common treatment is to make an incision (capsulotomy) into the capsule of the cloudy lens to surgically remove it. Two types of eye surgery can be used to remove cataracts: extra-capsular cataract extraction (ECCE) and intra-capsular cataract extraction (ICCE). ECCE surgery involves removing the lens, but leaving the majority of the lens capsule intact. High frequency sound waves (phacoemulsification) are sometimes used to break up the lens before extraction. ICCE surgery involves removing the lens and lens capsule, but it is rarely performed in modern practice. In either extra-capsular surgery or intra-capsular surgery, the cataractous lens is removed and replaced with an intraocular plastic lens (an intraocular lens implant) which stays in the eye permanently. The intraocular lens is placed into a cartridge and inserted through the small surgical incision. The inserter folds the intraocular lens and pushed it through a small needle. The end of the needle is positioned within the capsular bag. When the folded intraocular lens exits the end of the needle, it slowly unfolds as the surgeon manipulated the lens into its final position.

Cataract operations are usually performed using a local anesthetic, and the patient is allowed to go home the same day. Until the early twenty-first century intraocular lenses were always monofocal; since then improvements in intraocular technology allow implanting a multifocal lens to create a visual environment in which patients are less dependent on glasses. Such multifocal lenses are mechanically flexible and can be controlled using the eye muscles used to control the natural lens.

Complications are possible after cataract surgery, including endophthalmitis, posterior capsular opacification, and retinal detachment.

Laser surgery involves cutting away a small circle-shaped area of the lens capsule, enough to allow light to pass directly through the eye to the retina. There are, as always, some risks, but serious side effects are very rare. As of 2012, research into the use of extremely-short-pulse (femtosecond) lasers for cataract surgery was being carried out. High frequency ultrasound is currently the most common means to extract the cataract lens.

Cataract surgeries are conducted in an operating room under sterile conditions to prevent the risk of infection, particularly endophthalmitis; a rapid devastating infection that can cause blindness in a few days. The patient's eye is cleaned with an antiseptic, and then isolated with a sterile drape that fully covers the patient with only the eye exposed. A sterile field is established around the patient such that any personnel or instrumentation must be suitably scrubbed, draped or sterilized following standard aseptic procedures.

With reference to FIGS. 1 and 2, such a prior art type of cataract surgery includes using a surgical microscope to view the interior of the eye through a patient's cornea and iris. The surgeon typically makes two incisions 10, 12 in the patient's cornea, close to the limbus, to enable surgical instruments to gain access to the interior segment of the eye and to implant an intraocular lens after the cataract crystalline lens has been removed. For example, an intraocular lens inserter 14 can be inserted through the incision 10 and a positioning device 16 can be inserted through the incision 12.

The surgery typically includes creating a full-circle tear in the center of the capsular bag on the interior side, called a "capsulorhexis," and removing the torn circle of the capsule. Then, the cataract crystalline lens is removed using a phacoemulsifier, an ultrasonic infusing and aspirating instrument that breaks up the cataract and aspirates the fragments, removing the cataract.

The lingering cortical material that is attached to the inner surface of the capsular bag is then aspirated using an infusion/aspirating instrument. The intraocular lens 18 is then inserted using the lens inserter 14 and positioned within the capsular bag using the positioning device 16 or other devices.

The lens inserter 14 transfers the flat intraocular lens 18 through the small clear corneal incision 10 into the capsular opening (capsulorhexis) and to its final position within the capsular bag. The inserter 14 pushes the flat lens 18 through a cartridge which causes the lens to fold and pass through a tubular portion of the cartridge which is placed into the small incision 10. As the lens 18 emerges out of the tubular end of the cartridge 14, it slowly unfolds and returns to its original flat shape.

Recent advances in femtosecond laser instrumentation has automated the process of making entry incisions and the capsulorhexis as well as pre-cutting the cataract making the cataract surgical procedure more precise, safer, and easier for the surgeon to execute.

The majority of current lens inserters are manually operated re-usable instruments with primarily one of two methods to push the lens: a lead screw or plunger. The lead screw approach provides consistent and smooth delivery of the lens, however slowly, and requires the surgeon or an assistant to turn the manual lead screw as the surgeon positions the tip of the instrument.

The plunger approach does not require an assistant, as the surgeon uses their thumb to drive the lens forward, much like injecting a drug from a syringe. Additionally, the surgeon can more readily control the speed of delivery, swiftly moving though the less critical portions and slowing for the more delicate segments. A draw back of the plunger approach can emerge when the lens becomes stuck resulting in a more forceful push by the surgeon where upon clearance of the hang-up, the lens can over-shoot its exit and injure the patient.

Recently, efforts have been made to perform such lens replacement surgeries using smaller corneal incisions. For example, as shown schematically in the illustration of FIG. 3, typically, the distal end of an intraocular lens inserter 14 is inserted completely through the incision 10, during a procedure of inserting an intraocular lens 18.

However, with reference to FIG. 4, recently surgeons have been adopting a "wound-assist" technique, wherein only a small portion of the tip 20 of the intraocular lens inserter 14 is inserted into the incision 10, wherein the incision 10 is smaller than the incisions previously made, such as during the procedure illustrated in FIG. 3. As such, the intraocular lens 18, in its folded state, is pushed through and slides along interior surfaces of the incision 10. This allows the incision 10 to be smaller and the wound itself (incision 10) becomes a lumen for inserting the lens 18 into the eye.

During such a procedure, the surgeon can use the distal end 20 of the tip of the intraocular inserter 14 to help hold the incision 10 open. For example, the surgeon might apply a lateral force in the direction of arrow 22 in order to hold the incision 10 open such that the lens 18 can be pushed therethrough.

SUMMARY

The inventions disclosed herein generally relate to devices and methods for inserting intraocular lens into an eye of an animal and, more particularly for devices and methods that provide temperature compensation to lens inserters.

The devices, systems, and methods herein may provide temperature compensation for an IOL inserter system, such as those disclosed in the applications incorporated by reference herein. In one embodiment, the system uses the pressure of the fluid as the sensing output to control features that affect the output delivery rate of the IOL inserter.

In an exemplary embodiment, an IOL inserter system may include one or more of the following features enabling temperature compensation:
1. Using a fluid pressure sensing system to reduce the maximum valve opening by moving the actuator pivot.
2. Using a fluid pressure sensing system to reduce the maximum valve opening by moving the handle stop.
3. Using a fluid pressure sensing system to reduce the maximum valve opening by moving the valve seat.
4. Using a fluid pressure sensing system to reduce the maximum valve opening by acting on an elastomeric orifice.

5. Using a fluid pressure sensing system to reduce the maximum valve opening by closing one or more bi-stable bypass valves.
6. Using a fluid pressure sensing system to reduce the maximum valve opening by closing a variable orifice bypass valve.

In another embodiment, devices, systems, and methods may provide temperature compensation for an IOL inserter system, such as those disclosed in the applications incorporated by reference herein. In one embodiment, the system uses any temperature measuring as the sensing output to control features that affect the output delivery rate of the IOL inserter.

In an exemplary embodiment, an IOL inserter system may include one or more of the following features enabling temperature compensation:
1. Using a temperature sensing system to reduce the maximum valve opening by moving the actuator pivot.
2. Using a temperature sensing system to reduce the maximum valve opening by moving the handle stop.
3. Using a temperature sensing system to reduce the maximum valve opening by moving the valve seat.
4. Using a temperature sensing system to reduce the maximum valve opening by acting on an elastomeric orifice.
5. Using a temperature sensing system to reduce the maximum valve opening by closing one or more bi-stable bypass valves.
6. Using a temperature sensing system to reduce the maximum valve opening by closing a variable orifice bypass valve.

In still another embodiment, devices, systems, and methods may provide temperature compensation for temperature compensation for an IOL inserter system, such as those disclosed in the applications incorporated by reference herein. The system controls the output gas source pressure that affects the output delivery rate of the IOL inserter.

In an exemplary embodiment, an IOL inserter system may include one or more of the following features enabling temperature compensation:
1. Using a gas pressure measuring system to regulate the pressure of the gas source providing constant pressure to the fluid divider piston.

In yet another embodiment, devices, systems, and methods may provide temperature compensation for an IOL inserter system, such as those disclosed in the applications incorporated by reference herein. The system controls the maximum fluid flow that affects the output delivery rate of the IOL inserter.

In an exemplary embodiment, an IOL inserter system may include one or more of the following features enabling temperature compensation:
1. Using a temperature compensating flow control valve to limit the maximum fluid flow.
2. Using a pressure compensating flow control valve to limit the maximum fluid flow.
3. Using a temperature and pressure compensating flow control valve to limit the maximum fluid flow.

In accordance with an exemplary embodiment, an intraocular lens inserter is provided that includes an intraocular lens portion configured to receive an intraocular lens for insertion into an eye of an animal; and an actuator portion comprising a plunger for delivering an intraocular lens from the intraocular lens portion, a source of pressurized fluid, a valve, an actuator member coupled to the valve for selectively opening a flow path from the source to the plunger to control flow of the pressurized fluid to advance the plunger to deliver the intraocular lens at a desired rate, and a pressure feedback mechanism for limiting movement of the actuator member to reduce a maximum valve opening position of the valve as temperature rises.

In accordance with another embodiment, an intraocular lens inserter is provided that includes an intraocular lens portion configured to receive an intraocular lens for insertion into an eye of an animal; a plunger configured to contact the intraocular lens and discharge the intraocular lens from the intraocular lens portion; and means for limiting the transmission of energy from an energy storage device to the plunger as ambient temperature increases.

In accordance with still another embodiment, an intraocular lens inserter is provided that includes an intraocular lens portion configured to receive an intraocular lens for insertion into an eye of an animal; and an actuator portion comprising a plunger for delivering an intraocular lens from the intraocular lens portion, a source of pressurized fluid, a valve, an actuator member coupled to the valve for selectively opening a flow path from the source to the plunger to control flow of the pressurized fluid to advance the plunger and deliver the intraocular lens at a desired rate, and a pressure feedback mechanism for reducing a maximum valve opening position of the valve as temperature rises.

In accordance with yet another embodiment, an intraocular lens inserter is provided that includes an intraocular lens portion configured to receive an intraocular lens for insertion into an eye of an animal; and an actuator portion comprising a plunger for delivering an intraocular lens from the intraocular lens portion; a source of pressurized fluid; an actuator member coupled to a valve for selectively opening a flow path from the source to the plunger to control flow of the pressurized fluid to advance the plunger and deliver the intraocular lens at a desired rate; a valve seat movable relative to the valve; and an annular orifice member coupled to the valve seat defining a portion of the flow path, the valve seat coupled to the source such that increasing pressure within the source causes the valve seat to compress the orifice member to restrict flow therethrough and thereby reduce the maximum fluid flow to the plunger as temperature rises.

In accordance with another embodiment, an intraocular lens inserter is provided that includes an intraocular lens portion configured to receive an intraocular lens for insertion into an eye of an animal; an actuator portion comprising a plunger for delivering an intraocular lens from the intraocular lens portion; a source of pressurized fluid; a primary flow path from the source of pressurized fluid to the plunger; an actuator member coupled to a valve for selectively opening the primary flow path to control flow of the pressurized fluid to advance the plunger and deliver the intraocular lens at a desired rate; a bypass flow path from the source of pressurized fluid to the plunger; and a bypass valve for selectively closing the bypass flow path based on pressure feedback from the source of pressurized fluid.

In accordance with still another embodiment, a method for discharging an intraocular lens that includes providing an intraocular lens inserter comprising an intraocular lens and an actuator including a source of pressurized fluid and an actuator member coupled to a valve; and manipulating the actuator member to open the valve and deliver pressurized fluid from the source to a plunger to advance the plunger and discharge the intraocular lens, wherein movement of the actuator member is limited as pressure within the source increases.

In accordance with still another embodiment, a method for discharging an intraocular lens that includes providing an intraocular lens inserter comprising an intraocular lens and an actuator including a source of pressurized fluid and an actuator member coupled to a valve; and manipulating the actuator member to open the valve and deliver pressurized fluid from the source to a plunger to advance the plunger and discharge the intraocular lens, wherein fluid flow is controlled at least in part based on pressure within the source to provide temperature compensation.

In accordance with still another embodiment, an intraocular lens inserter comprising an intraocular lens portion configured to receive an intraocular lens for insertion into an eye of an animal; and an actuator portion comprising a plunger for delivering an intraocular lens from the intraocular lens portion; a source of pressurized fluid; a primary flow path from the source of pressurized fluid to the plunger; an actuator member coupled to a valve for selectively opening the primary flow path to control flow of the pressurized fluid to advance the plunger and deliver the intraocular lens at a desired rate; a bypass flow path from the source of pressurized fluid to the plunger; and a bypass valve for selectively closing the bypass flow path based on pressure feedback from the source of pressurized fluid.

In accordance with still another embodiment, a method for discharging an intraocular lens, comprising providing an intraocular lens inserter comprising an intraocular lens and an actuator including a source of pressurized fluid and an actuator member coupled to a valve; manipulating the actuator member to open the valve and deliver pressurized fluid from the source along a primary flow path to a plunger to advance the plunger and discharge the intraocular lens, wherein the intraocular lens inserter comprises a first bypass flow path from the source to the plunger and a first bypass valve coupled to the source such that, when pressure within the source exceeds a predetermined threshold, the first bypass valve limits flow through the first bypass flow path to provide temperature compensation.

A pressure feedback mechanism may include a port communicating with the source of pressurized fluid, and a piston may be movable within the port and coupled to the actuator member to limit movement of the actuator member based on pressure within the source of pressurized fluid. A piston may be coupled to the actuator member to move a pivot of the actuator member and thereby reduce range of motion of the actuator member and thereby reduce the maximum valve opening position of the valve as pressure within the source of pressurized fluid increases as the temperature rises. An energy storage device for providing pressure to the source of pressurized fluid may be included. A source of pressurized fluid may include a chamber including incompressible fluid. An energy storage device may include a piston communicating with the chamber and biased to apply a predetermined pressure to the chamber via the piston. An energy source may include one of a canister of pressurized gas and a spring for biased the piston. A source of pressurized fluid may include a chamber including viscous fluid. An energy storage device may include a canister of pressurized compressible fluid and a piston communicating with the chamber such that compressible gas from the canister applies a predetermined pressure to the chamber via the piston. A source of pressurized fluid may include a chamber within the actuator portion that includes an incompressible, viscous fluid.

A pressure feedback mechanism may include a valve seat movable relative to the valve and coupled to the source such that increasing pressure within the source causes the valve seat to move the valve and thereby reduce the maximum valve opening position of the valve as temperature rises. A bypass valve may be configured to close the bypass flow path when the pressure exceeds a first predetermined threshold. An intraocular lens inserter may include a second bypass flow path from the source of pressurized fluid to the plunger; and a second bypass valve for selectively closing the second bypass flow based on pressure feedback from the source of pressurized fluid. A second bypass valve may be configured to close the second bypass flow path when the pressure exceeds a second predetermined threshold different than the first predetermined threshold. A bypass valve is configured to gradually close the bypass flow path as pressure within the source of pressurized fluid increases.

A first bypass valve may close the bypass path to first fluid flow when the pressure exceeds the predetermined threshold. A first bypass valve may increasingly limit flow through the first bypass path as the pressure exceeds the predetermined threshold. A second predetermined threshold may be higher than the first predetermined threshold.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 14 is an enlarged perspective and exploded view of the inserter shown in FIG. 13.

FIG. 15 is an enlarged side elevational view of a lens cartridge removed from the lens cartridge holding portion.

FIG. 16 is a view of the inserter of FIG. 15 with the lens cartridge inserted into the lens cartridge holder portion.

DETAILED DESCRIPTION OF THE EXEMPLARY EMBODIMENTS

Figure 1:
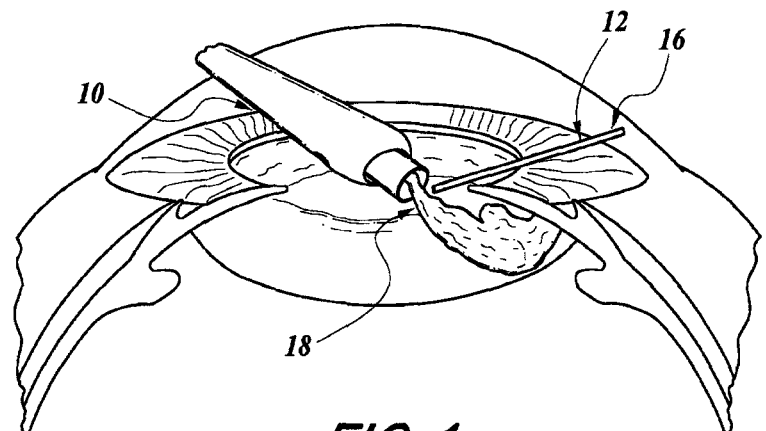
FIG. 1 is an enlarged sectional view of a human eye with an intraocular lens inserter inserted through an incision in the cornea and a positioning device inserted through a second incision, with an intraocular replacement lens shown as being partially ejected from the intraocular lens inserter.
Figure 2:
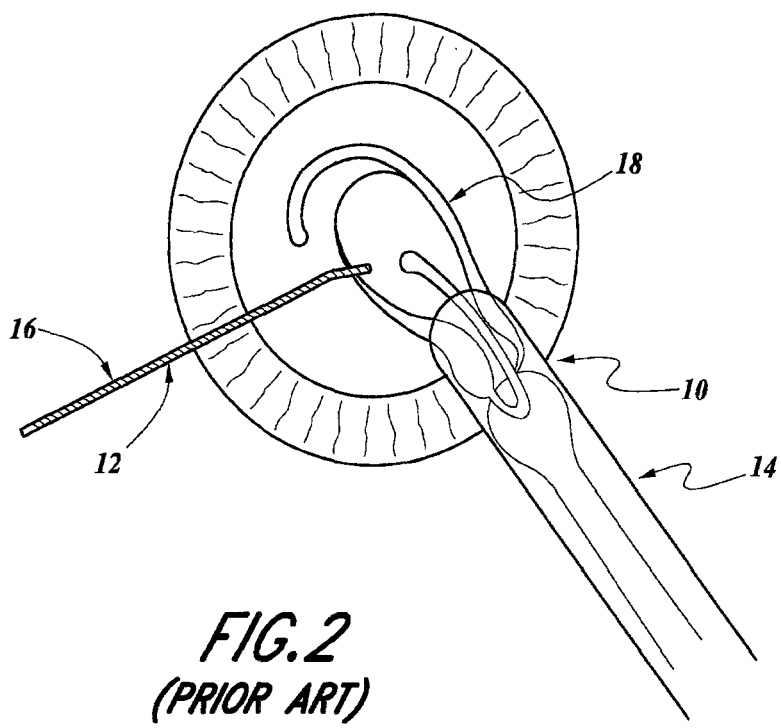
FIG. 2 is a front plan view of the procedure illustrated in FIG. 1.
Figure 3:
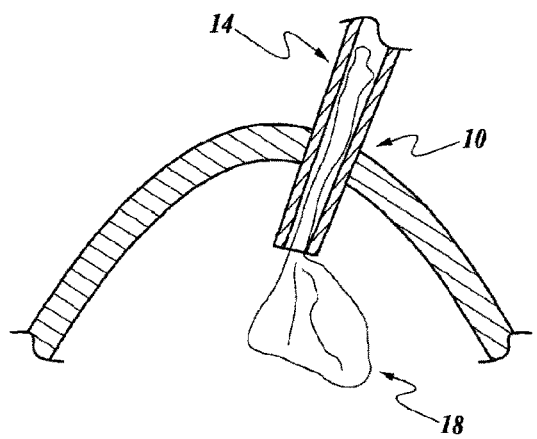
FIG. 3 is a schematic diagram of a portion of the arrangement shown in FIG. 1, with the distal tip of an intraocular lens inserter inserted completely through an incision and discharging a replacement lens.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the proceeding technical field, background, brief summary, or the following detailed description.

Certain terminology may be used in the following description for the purpose of reference only, and thus are not intended to be limiting. For example, terms such as "upper," "lower," "above," and "below" refer to directions in the drawings to which reference is made. Terms such as "proximal," "distal," "front," "back," "rear," and "side" describe the orientation and/or location of portions of the component within a consistent but arbitrary frame of reference, which is made clear by reference to the text and the associated drawings describing the component under discussion. Such terminology may include the words specifically mentioned above, derivatives thereof, and words of similar import.

As used herein, the terms "front" and "distal" refer to the parts of the subject apparatus that are located further away from the user (e.g., surgeon) of the apparatus during an injection operation. As used herein, the terms "rear" and "proximal" refer to the parts of the apparatus which are located closer to the user (e.g., surgeon) of the apparatus during an injection operation.

The inventions disclosed herein are described in the context of intraocular lens inserters for the treatment of cataracts. However, the inventions disclosed herein can be used in other context as well with regard to surgical devices that are required to discharge devices, for example, into or beyond the tissues of an animal, such as a human.

Figure 5:
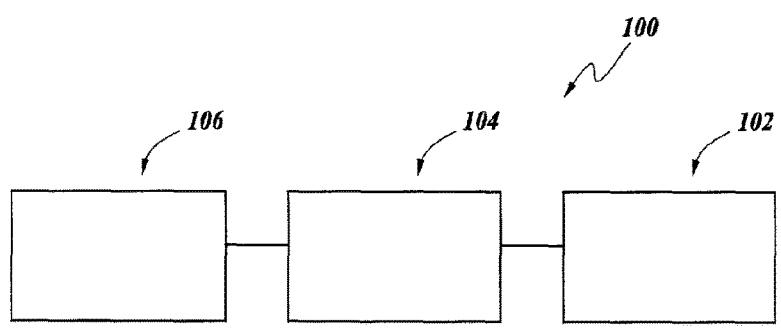
FIG. 5 is a schematic illustration of an embodiment of an intraocular lens inserter.

With reference to FIG. 5, an intraocular lens inserter 100 can include an energy storage device 102, an actuator device 104, and a lens discharge portion 106. The energy storage portion 102 can be in the form of any type of energy storage device. In some embodiments, the energy storage portion 102 is in the form of a device for storing a compressible fluid, mechanical springs, or other compressible types of energy storage devices. In some embodiments, the energy storage portion 102 can be configured to discharge mechanical energy from the energy stored therein. For example, where the energy storage device 102 is in the form of a compressed gas container, the energy storage device 102 can discharge such compressed gas which therefore provides an output of mechanical energy.

The actuator portion 104 can be any type of actuator configured to provide controllable actuation of the output of mechanical energy from the energy storage portion 102. For example, in some embodiments, the actuator portion 104 can be in the form of a mechanical or electronic button or lever for providing a user with means for controlling the output of mechanical energy from the energy storage portion 102. For example, the actuator 104 can be in the form of a button or other electronic devices configured to provide variable resistance or movement associated with a mechanical member used for outputting the energy from the energy storage portion 102. The actuator portion 104 can also provide for the control of an output member configured for interaction with the intraocular lens portion 106. For example, the actuator portion 104 can include an output plunger or other device for interacting with the intraocular lens portion.

The intraocular lens portion 106 can be configured to interact with or retain an intraocular lens cartridge which is widely commercially available from several different sources. For example, the intraocular lens portion 106 can be configured to releasably engage with an intraocular lens cartridge commercially available as a Monarch available from Alcon. The intraocular lens portion 106 can also be configured to move between an open position configured for allowing an intraocular lens cartridge to be engaged with the lens portion 106 and a closed portion in which the lens portion 106 engages with the lens cartridge.

As such, in operation, the actuator portion 104 can be manipulated by a user, such as a surgeon, to control the output of mechanical energy from the energy storage portion 102, to thereby control the discharge of a lens from a lens cartridge retained by the lens portion 106. Further, the inserter 100 can be configured to be hand-held, and in some embodiments, disposable.

As explained elsewhere herein, viscosity and/or other properties of the fluid in such storage devices may change with temperature, which may modify the performance characteristics of the actuator. Optionally, one or more devices may be included that at least partially compensate for such changes in the fluid, e.g., by providing feedback to the actuator based on pressure of the fluid and/or providing one or more valves, pressure regulators, and/or other features that limit opening a valve from the energy storage device and/or the limit delivery rate available using the actuator.

With reference to FIGS. 6-18, a further embodiment of the lens inserter 100 is illustrated there and identified by the reference number 100A. The features and components of the lens inserter 100A that can be the same or similar to corresponding components of the lens inserter 100 have been identified with the same reference numeral, except that the letter "A" has been added thereto.

Figure 6:
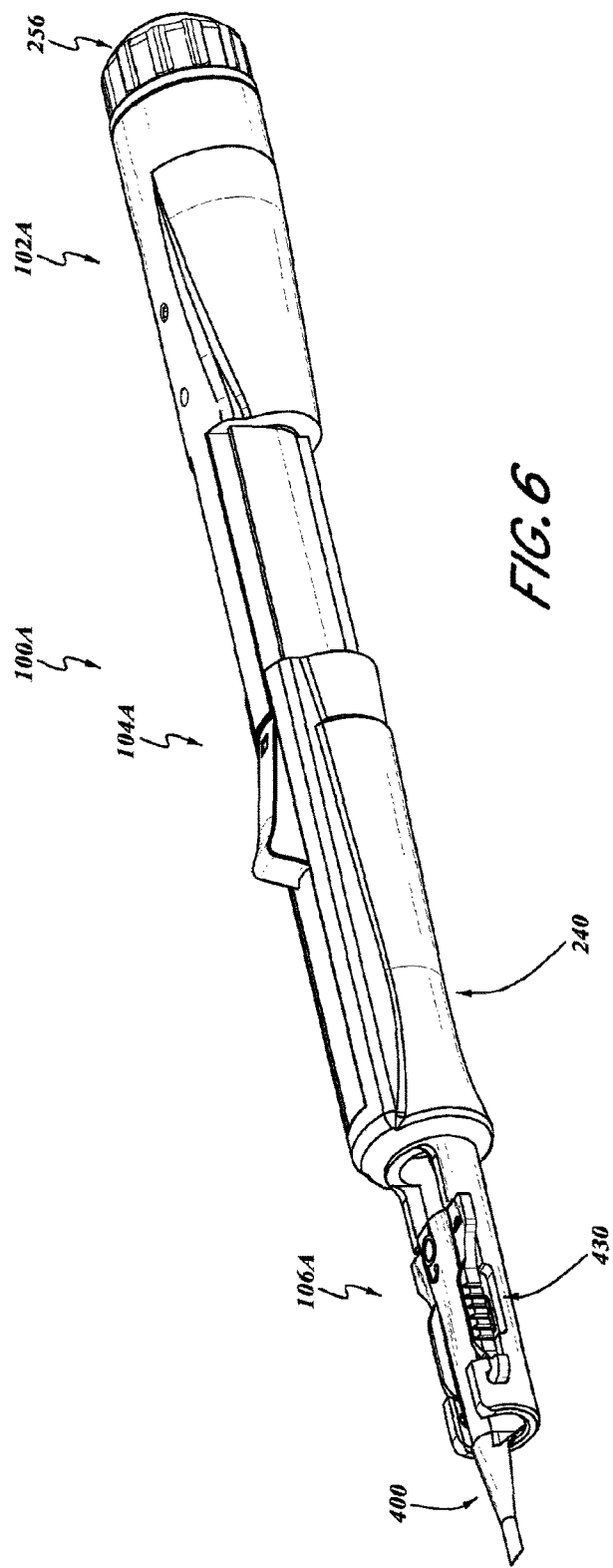
FIG. 6 is a perspective view of a further embodiment of an intraocular lens inserter.
Figure 7:
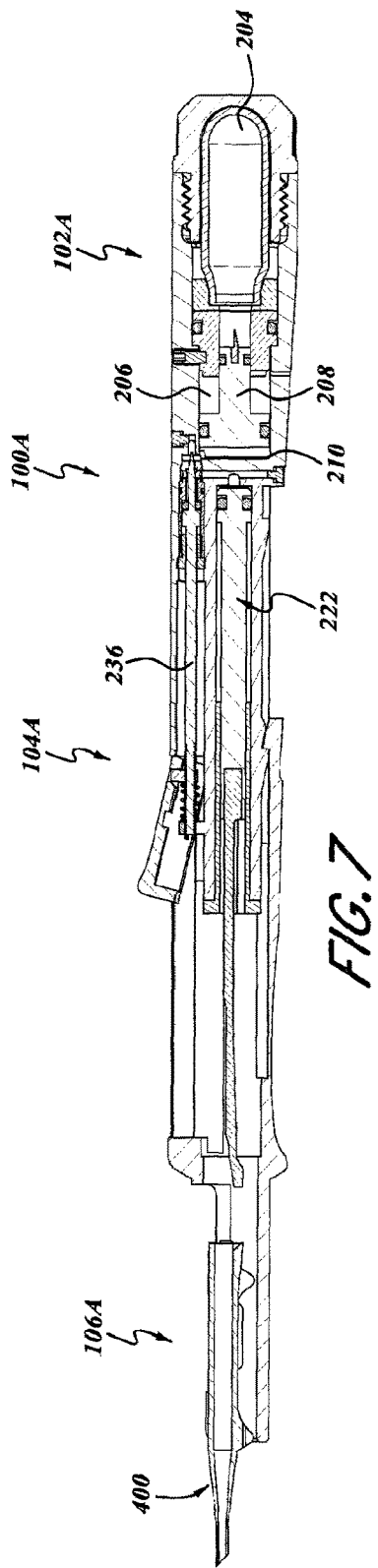
FIG. 7 is a side elevational and cross-sectional view of the intraocular lens inserter of FIG. 6.
Figure 8:
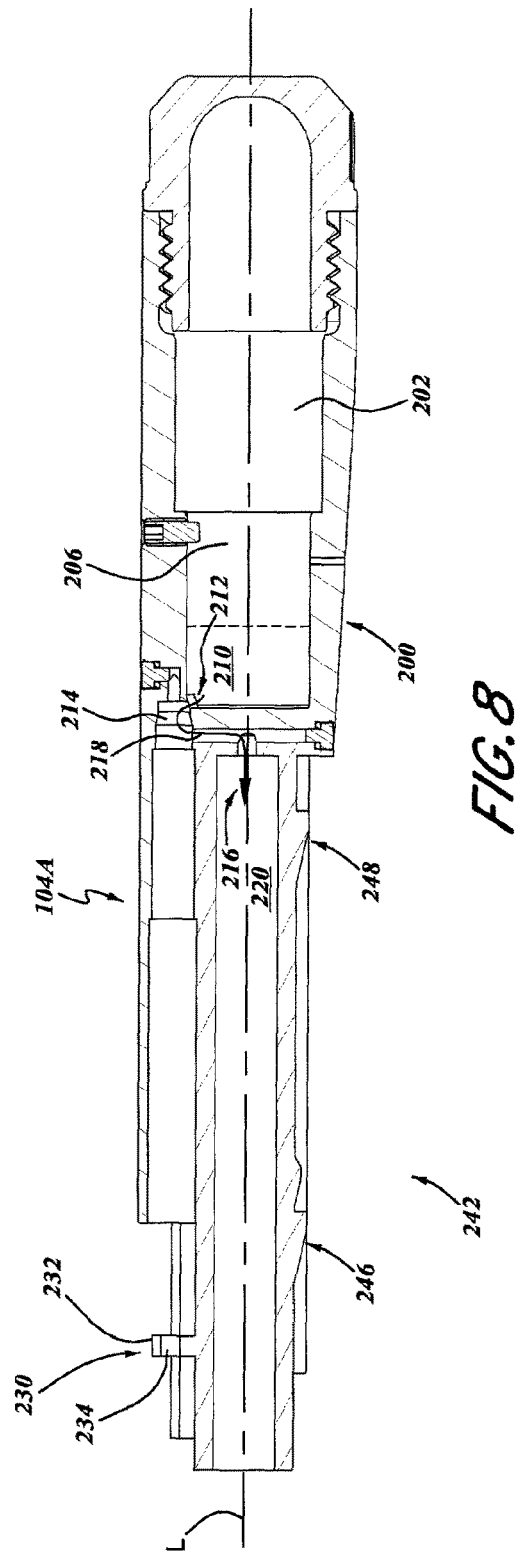
FIG. 8 is a side elevational and cross-sectional view of a portion of a housing member of the intraocular lens inserter of FIG. 7.

With reference to FIGS. 6-8, the intraocular lens inserter 100A also includes an energy storage portion 102A, an actuator portion 104A, and a lens portion 106A.

In the illustrated embodiment, with reference to FIG. 8, the inserter 100A includes a main body portion 200 which includes various cavities, recesses, and conduits, and, in the present embodiment, provides for communication between the energy storage portion 102A and the actuator portion 104A. FIG. 8 illustrates the body portion 200 with all other components removed therefrom. In some embodiments, optionally, the body portion 200 can be made from a single piece of material forming a monolithic body. However, other configurations can also be used.

In some embodiments, the body portion 200 includes an energy storage receiving portion 202. In some embodiments, the receiving portion 202 is configured as a recess within the body 200, sized and configured to receive a container of compressed gas. In some embodiments, the recess 202 can be sized to receive a canister, cartridge, or other container of compressed carbon dioxide 204. Such containers of compressed gas and, in particular, carbon dioxide, are widely commercially available.

The housing 200 can also include a piston chamber 206 configured to receive gas discharged from the canister 204. The piston chamber 206 can include devices for interacting with the gas from the canister 204 for providing usable mechanical energy. For example, as shown in FIG. 7, a piston 208 can be disposed in the piston chamber portion 206. In some embodiments, the piston 208 subdivides the piston chamber portion 206 into a gas-receiving portion and a liquid-receiving portion 210.

The housing 200 can also include a conduit 212 connecting the energy storage portion 102A with the actuator portion 104A. For example, the conduit 212 can provide a flow path between the liquid receiving portion 210, along the direction of arrow 216, into the actuator portion 104A.

The conduit 212 can include an aperture in a portion of the liquid-receiving portion 210, that leads into an actuator control portion 214, then to a lateral connector portion 218, into a further liquid-receiving portion 220 of the actuator portion 104A.

The actuator receiving portion 214 can be configured to receive an actuator for controlling the flow of fluid along the conduit 212. Additionally, the chamber 220 can be configured to receive a piston 222, described in greater detail below.

With continued reference to FIG. 8, the body 200 can also include an actuator mounting portion 230. The actuator mounting portion 230 can be in the form of a projection 232 extending radially outwardly from the longitudinal axis L of the body 200. The projection 232 can include an aperture 234 and could be configured to receive an actuator rod 236 (FIG. 7).

The body 200 can also include various other outer surfaces and devices for engagement with a sliding cartridge engagement member 240 (FIG. 6), described in greater detail below. For example, the outer surface 242 of the actuator portion 104A of the body 200 can include various engagement devices 246, 248, and/or other ridges for providing alignment and engagement with the engagement device 240. Such features are described in greater detail below with reference to FIG. 14.

Figure 9:
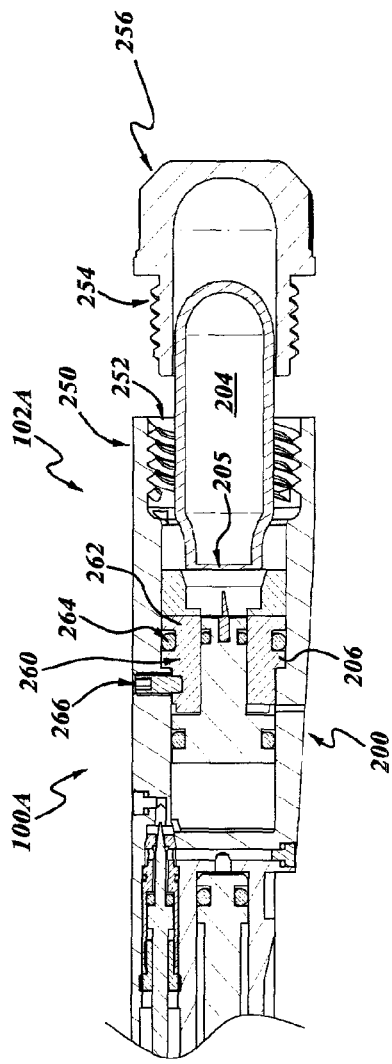
FIG. 9 is an enlarged sectional view of an energy storage portion of the lens inserter of FIG. 6 and in a partially exploded view.
Figure 10:
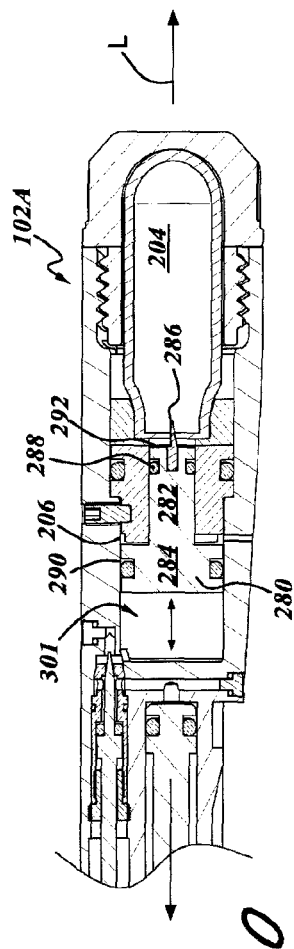
FIG. 10 is also a cross-sectional view of lens inserter of FIG. 6 showing an energy storage device being pierced by a piercing device and within end caps screwed down over the energy storage device.
Figure 11:
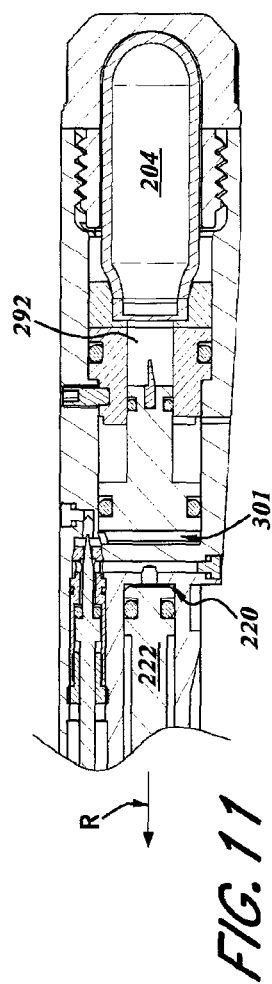
FIG. 11 is a cross-sectional view of the inserter of FIG. 6 showing movement of a piston after an expanding gas has been discharged from the energy storage device.

With reference to FIGS. 9-11, the storage portion 102A is illustrated in further detail, including various components that can be included within the body member 200. The distal end 250 of the body member 200 can include internal threads 252 configured for engagement with external threads 254 disposed on a removable end cap 256.

Additionally, the energy storage portion 102A can include a bulkhead member 260. The bulkhead member 260 can be configured to provide for secure engagement with a chosen energy storage device used with the energy storage portion 102a. As noted above, the illustrated embodiment is designed for use with a canister of compressed carbon dioxide 204. Thus, in the illustrated embodiment, the bulkhead member 260 includes an upstream end 262 configured for abutting engagement with a distal end 205 of the canister 204. The bulkhead member 260 can also include a sealing device, such as an O-ring 264, for providing a sealing engagement with an inner surface of the piston chamber 206. In the illustrated embodiment, the bulkhead member 260 remains stationary during operation. Thus, the inserter 100a also includes a set screw 266 which extends through the body portion 200 for secure engagement with the bulkhead member 260. Other designs can also be used.

The energy storage portion 102A can also include an accumulator piston 280. In the illustrated embodiment, the accumulator piston 280 is slidably engaged with two surfaces. Firstly, the accumulator piston 280 includes a first portion 282 engaged with an inner surface of the bulkhead member 260 and a downstream portion 284 engaged with an inner surface of the piston chamber 206. Additionally, in the illustrated embodiment, the piston 280 includes a piercing needle 286 that is configured to pierce a seal that is commonly used on compressed gas cartridges, such as the carbon dioxide compressed gas canister 204.

The piston 280 is configured to move slidably along the longitudinal axis L of the inserter 100A. As such, the piston 280 includes an O-ring 288 for sealing against the inner surface of the bulkhead 260 and a second O-ring 290 for providing a sliding seal with the inner surface of the piston chamber 206.

In some embodiments, the O-ring seal 288 can be configured to maintain all of the gas discharged from the canister 204 in the area 292 disposed between the piston 280 and the canister 204. Additionally, the piston chamber 206 can be configured to receive a substantially incompressible fluid, such as a liquid, including but not limited to, silicone oil, propylene glycol, glycerin, saline, water, or other substantially incompressible fluids. For purposes of illustration, the piston 280 and the downstream or distal portion of the piston chamber 206 can be considered as a substantially incompressible fluid-receiving chamber 301. Thus, in some embodiments, the O-ring 290 is configured to maintain any liquid or fluid in the chamber 301 in the distal portion of the chamber 206.

During operation, when the cap 256 is screwed into the threads 252, the canister 204 is thereby pushed into the piercing needle 286, thereby opening the canister 204 and releasing the compressed gas therein into the space between the canister 204 and the bulkhead 260 and the distal proximal end portion 282 of the piston 280.

With reference to FIG. 11, when the actuator portion 104A is operated appropriately, the pressurized gas from the canister 204 continues to expand into the gas-receiving portion 292, thereby pressurizing any fluid or liquid in the substantially incompressible fluid receiving portion 301. Actuation of the actuator portion 104A allows the pressurized fluid in the chamber 301 to flow outwardly therefrom and into the chamber 220 to thereby drive the piston 222 longitudinally in the direction of arrow R (FIG. 11), described in greater detail below.

Figure 12:
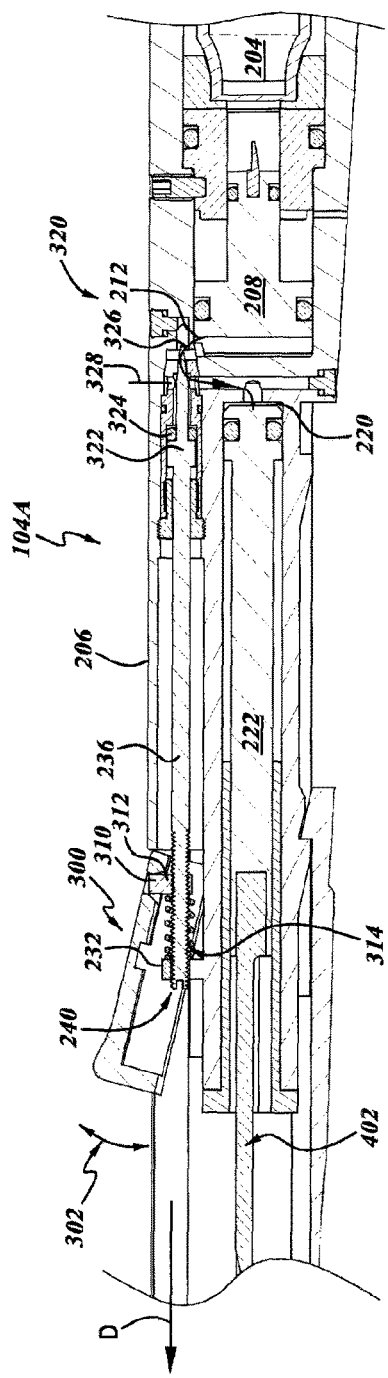
FIG. 12 is an enlarged sectional view of an actuator portion of the inserter of FIG. 6.

With continued reference to FIG. 12, the actuator portion 104A can include a lever or other actuator member 300 mounted relative to the housing member 200 so as to be movable between an unactuated position (illustrated in FIG. 12) and an actuated position (not shown). For example, the lever member 300 can be attached to the housing 200 with the hinge member (not shown), such that the actuator member can be pivotable along the arc 302. The lever member 300 can also be engaged with the rod 236 which can be configured to provide a flow control function for controlling the flow of substantially noncompressible fluid from the chamber 301 toward the chamber 220 for moving the piston 222. For example, the piston rod 236 can include a distal end 240 which extends through the aperture 234 of the projection 232 and a proximal end 320 configured to provide a flow control function.

The distal end 240 of the rod 236 can include a slot for engagement with a screwdriver to provide adjustment of the positioning of the rod 236. For example, the lever member 300 can also include an engagement member 310 pivotally mounted to the lever member 300. The engagement member 310 can include a threaded portion 312 configured for engagement with external threads on the distal portion 240 of the rod 236.

Additionally, a spring 314 can provide a bias of the lever member 300 to the unactuated position. Connected as such, when the lever mover 300 is moved through the arc 302, and more particularly, when the lever member 300 is moved downwardly from the position illustrated in FIG. 12, the engagement member pulls the rod 236 in a distal direction D, thereby moving the flow control portion 320 in the direction of arrow D. The spring 314 provides a bias return action for returning the lever member 300 to the position illustrated in FIG. 12, when released by a user.

With continued reference to FIG. 12, the proximal portion 320 of the rod 236 can include a piston member 322 and seal, in the form of an O-ring 324. The proximal portion 320 can also include a needle portion 326 configured to cooperate with a throat portion 328. Using well known techniques, the engagement and cooperation of the needle portion 326 with the throat portion 328 can be used to control a flow of substantially incompressible fluid along the conduit 212. For example, when the lever member 300 is moved downwardly from the position illustrated in FIG. 12, the piston rod is moved distally in the direction D, thereby moving the needle portion 326 also in the direction of arrow D, thereby forming or increasing a gap between the needle portion 326 and the throat portion 328. As such, fluid flows through the conduit 212, for example, a substantially incompressible fluid pressurized by the piston 208 due to interaction with gas discharged from the canister 204 can thereby flow through the conduit 212 toward the piston 222.

Figure 13:
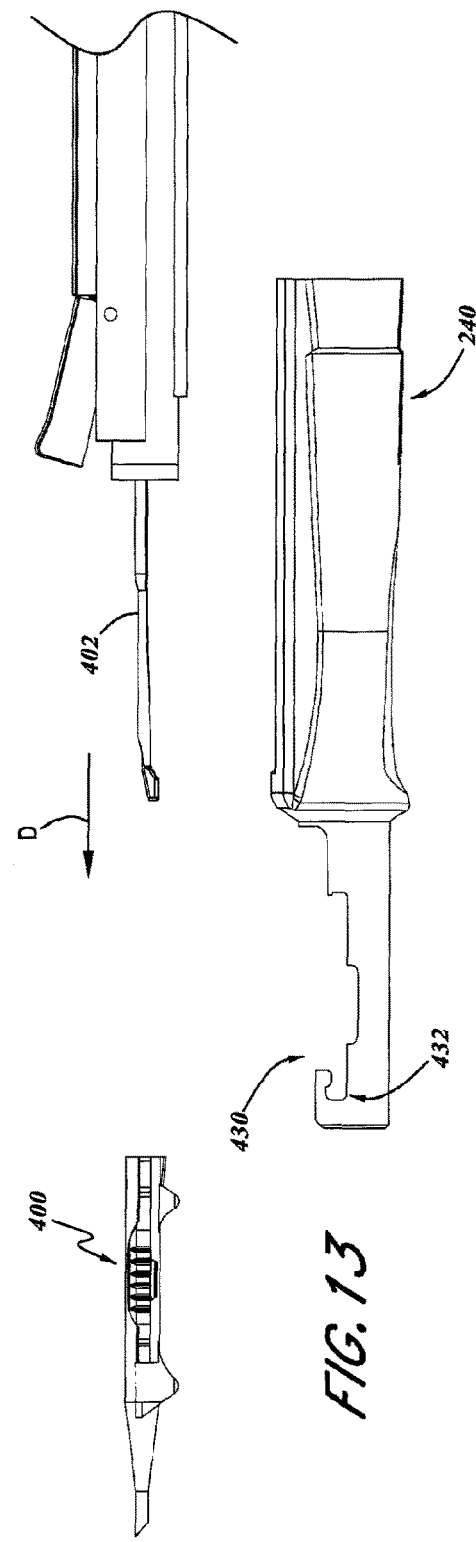
FIG. 13 is an exploded view of a lens cartridge holder portion of the inserter of FIG. 6.

When the substantially incompressible fluid presses against the piston 222, the piston 222 also moves in the direction of arrow D. This movement of the piston 222 can be used to discharge a lens from the cartridge 400. More specifically, as illustrated in FIGS. 12 and 13, a plunger 402 can be attached to a distal end of the piston 222. Thus, as the piston 222 is moved by the flow of fluid through the conduit 212, the plunger 402 is also moved in the direction of arrow D. This movement of the plunger 402 can be used to discharge a lens disposed within the cartridge 400, in a technique that is well known in the art.

With reference to FIGS. 13 and 14, the cartridge engagement member 240 can include a cartridge receiving portion 430. For example, the cartridge receiving portion 430 can include a distal wing engagement portion 432 and a body receiving portion 434. The wing receiving portion 432 and the body receiving portion 434 can be sized in accordance with the outer dimensions of commercially available lens cartridges 400, which are well known in the art.

The distal wing receiving portion 432 can include a recess designed to engage the wings 436 of the lens cartridge 400. Thus, when the cartridge 400 is engaged with the cartridge receiving portion 430, as shown in FIG. 6, the cartridge 400 is generally aligned with the plunger 402.

With continued reference to FIGS. 15 and 16, the cartridge receiving portion 430 can optionally include a proximal engaging portion 440 configured to engage with a proximal portion of the cartridge 400. For example, in some commercial embodiments of the cartridge 400, the cartridge 400 includes rearward wings 442 or other rearward surfaces. The cartridge engagement portion 430, therefore, can include an additional proximal recess 444 and an engagement device 446, for a positive engagement with the wings 442. Thus, as shown in FIG. 16, when the cartridge 400 is engaged both with the forward engagement portion 432 and the rearward engagement portion 444, with the projection 446 extending over the rearward wings 442, the cartridge 400 is more securely seated within the cartridge receiving portion 430.

Figure 4:
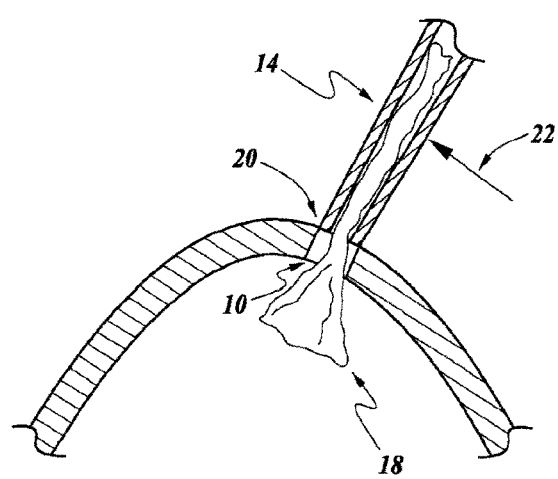
FIG. 4 is a schematic illustration of a different procedure than that illustrated in FIG. 3, in which the distal tip of the intraocular lens inserter is inserted only partially into the incision.

This can provide a substantial benefit to a surgeon using the inserter 100a. For example, with the projection 446 extending over the rearward wing 442, if the surgeon applies a force to the inserter 100a, in the direction of arrow F (FIG. 16), a torque T can be created or imparted onto the cartridge 400, thereby tending to cause the cartridge to pivot about the distal receiving portion 432, which can thereby tend to cause the proximal end of the cartridge 400 to lift upwardly in the direction of arrow U. However, the engagement portion 446 can help retain the proximal portion of the cartridge 400 within the receiving portion 430. This type of force can be created during execution of surgical procedures that are becoming more common, such as that described above with reference to FIG. 4, known as the "wound-assist" technique.

With continued reference to FIGS. 14-18, the member 240 can also be slidably engaged with the body 200. Thus, the member 240 can include various internal surfaces configured to cooperate with outer surfaces of the body 200. Thus, the member 240 can be slid longitudinally along the body 200, parallel to the longitudinal axis L of the inserter 100a.

Figure 17:
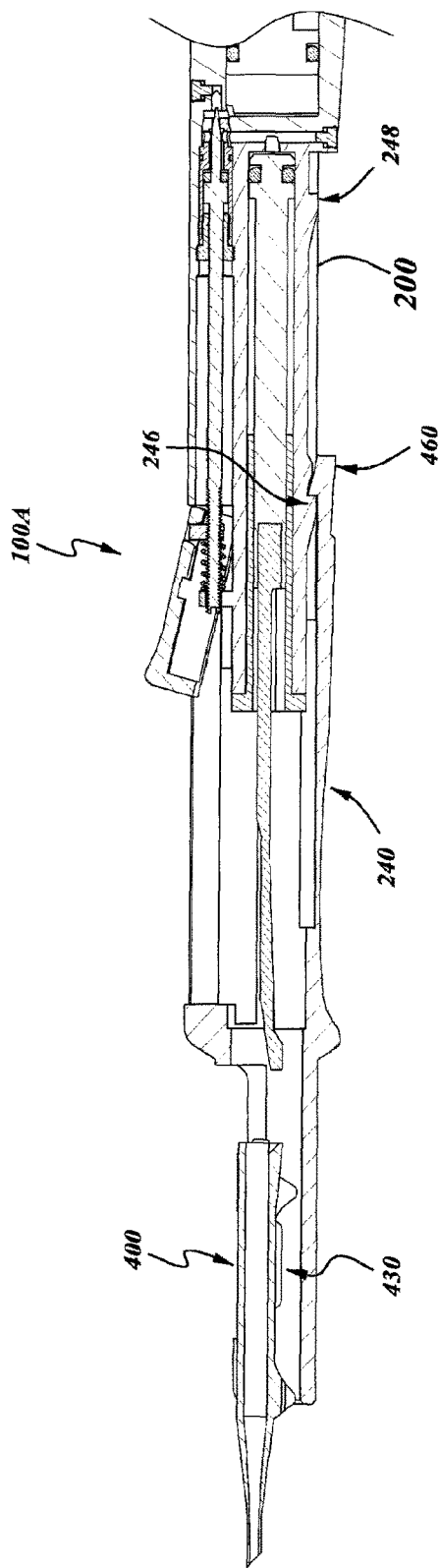
FIG. 17 is a partial cross-sectional view of the inserter of FIG. 16 prior to the lens cartridge being engaged with a plunger.
Figure 18:
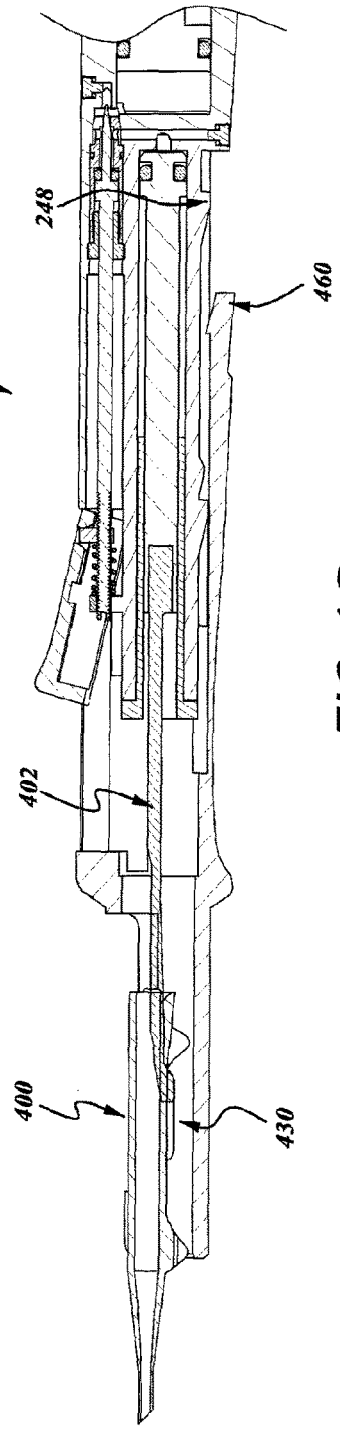
FIG. 18 is a cross-sectional view of the inserter shown after the lens holder portion has been moved axially to engage the plunger with the lens cartridge.

For example, with reference to FIGS. 17 and 18, the portion 240 can be moved to a distal position, show in FIG. 17. In this position, the lens receiving portion 430 is spaced apart from the plunger 402. As such, the cartridge 400 can be inserted into the cartridge receiving portion 430 without interference of the plunger 402. Thus, after the cartridge is received as such, as shown in FIG. 18, the portion 240 can be slid backwards relative to the body 200 until the plunger 402 engages or presses against a lens within the cartridge 400.

As noted above, the body 200 can include various detents or ramps or other portions 246, 248 which can engage with a portion of the member 240 for providing positive engagement into various positions. For example, the portion 240 can include a ramp and hook portion 460 configured to engage with the portion 246 and portion 248 of the housing member 200. Thus, the member 240 can be positively engaged in the position illustrated in FIG. 17 with the body member 200, and then when pulled in the proximal direction, so as to move the plunger 402 into the cartridge 400, the portion 460 can engage with the proximal portion of the housing 200 to thereby engage into a retracted position. Other designs can also be used to provide for the convenient insertion and removal of the cartridge 400.

Optionally, a lens inserter and/or other actuated device using pressurized fluid as an energy source may include one or more components to compensate for temperature changes that may otherwise affect the device. For example, with respect to the inserter device 100A shown in FIGS. 6-18, as the device is configured, the flow rate of the viscous fluid within the chamber 301 and hence the IOL delivery rate can vary as temperature changes.

Two physical properties that are temperature dependent contribute to this change are the dynamic viscosity of the viscous fluid and the vapor pressure of the gas.

In general, the laminar pipe flow rate, Q is driven by the following equation where r is the radius of the pipe, π is pi, L is the length of the pipe, ΔP is the pressure differential across the pipe, and μ is the dynamic viscosity.

$$Q = \frac{r^4 \pi}{8L} * \frac{\Delta P}{\mu}$$

As evident from the equation, the flow rate varies linearly with ΔP and inversely with μ.

For the IOL inserter drive system, the viscosity of the silicone or other fluid decreases as temperature increases and the vapor pressure of the gas increases with temperature. Therefore, the contribution of each of these elements add to increase the flow rate of the fluid and hence the IOL delivery rate.

Typical operating room temperatures where IOLs are inserted can vary from 17° C. to 26° C. where the vapor pressure the propellant gas, $CO_2$ varies from 5.3 to 6.6 mPa while the dynamic viscosity varies from 2440 to 2016 mPa/s. The total IOL delivery rate increases 50% from 17° C. to 26° C.

It may be desirable for the IOL delivery rate to remain substantially constant across the temperature range so that the surgical experience is consistent. Compensation means that limit the speed as the temperature increases may therefore be desirable. Several methods to achieve this compensation are described herein.

Figure 19:
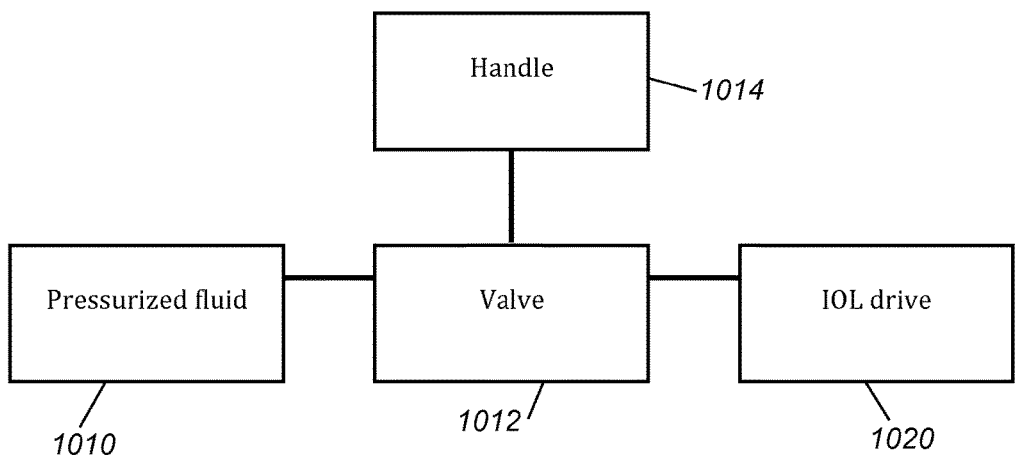
FIG. 19 is a schematic showing a configuration for an actuator for a lens inserter that opens a valve to a pressurized fluid to deliver a replacement lens from the inserter.

FIG. 19 shows an exemplary configuration of an actuator for an intraocular lens inserter drive 1020 that includes a source of pressurized fluid 1010, a valve 1012 for delivering fluid from the source 1010 to the drive 1020, and a handle or other actuator member 1014 for selectively opening the valve 1012 to deliver a desired pressure from the source 1010 to advance the drive 1020 at a desired rate, e.g., as described with reference to the inserter 100A. As a result, the speed of advancement vs. handle position may be linear or higher order response depending on the valve configuration.

Figure 20:
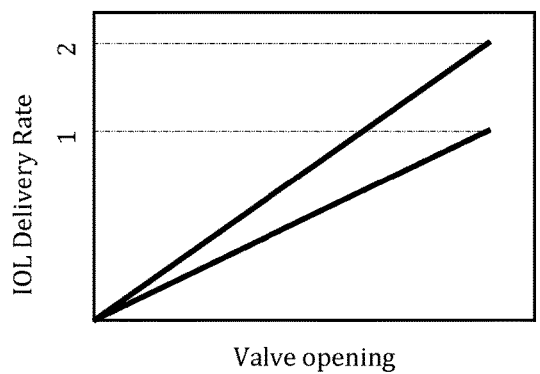
FIG. 20 is a graph showing the impact temperature can have on the actuator of a typical linear response inserter, such as that shown in FIG. 19, to increase the maximum delivery rate.

FIG. 20 shows the impact temperature has on a typical linear response inserter. The black (lower) line represents an inserter at the low end of the temperature range and the grey (upper) line represents the inserter at the high end of the temperature range. For the same control range of the handle, the maximum delivery rate increases from 1 to 2.

Figure 21:
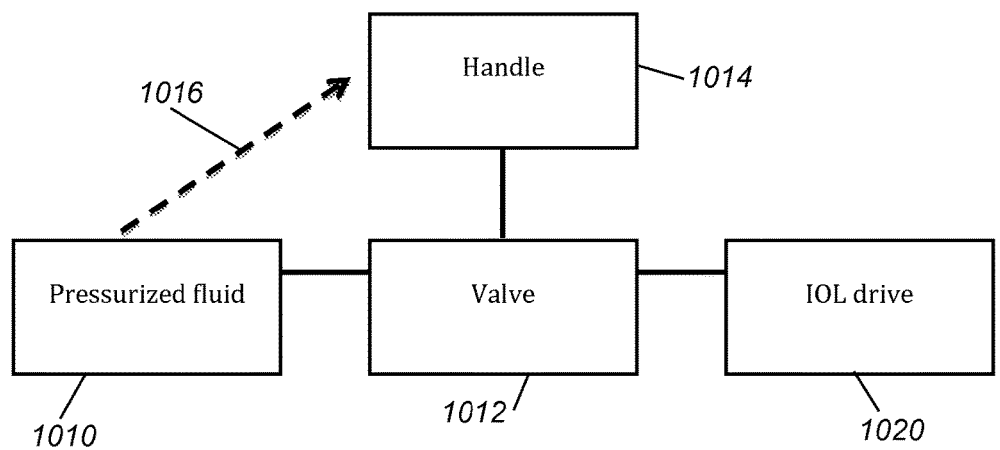
FIG. 21 is a schematic showing another configuration for an actuator for a lens inserter that opens a valve to a pressurized fluid to deliver a replacement lens in which pressure of the fluid is used as feedback to the actuator.

To provide a substantially constant maximum delivery rate, compensating for the effects of the temperature change, the pressure of the pressurized fluid within the source 1010 may be used to act on either the handle 1014 or the valve 1012 to reduce the maximum valve opening as the temperature rises. For example, as shown in FIG. 21, pressure 1016 from the fluid may be used as feedback to the handle 1014 (dashed line) or the valve 1012 (dotted line).

Figure 22:
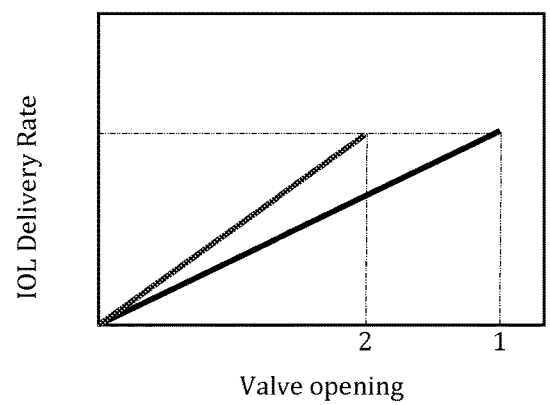
FIG. 22 is a graph showing how pressure feedback can limit the maximum delivery rate.

FIG. 22 shows exemplary effects that may result using the pressure feedback to limit the maximum valve opening where the maximum valve opening is limited to position 2 at high temperature, thereby limiting the maximum IOL delivery rate. As can be seen in the graph of FIG. 22, the maximum IOL maximum delivery rate may remain substantially the same.

FIGS. 23-27 show schematics of exemplary embodiments in which fluid pressure is used to provide feedback to an actuator for a lens inserter or other device, e.g., to limit movement of a handle and thereby limit maximum valve opening. Generally, the actuator 500 includes viscous fluid within a chamber 510, a valve 512 for delivering the fluid to a drive (not shown), and a handle 514 coupled to the valve 512 for selectively opening and closing the valve 512. In addition, a source of pressurized gas 516 is provided for compressing the fluid, e.g., based on pressure applied by the gas to the chamber 510 via piston 518. In the exemplary embodiment of the inserter 100A shown in FIGS. 6-18, the chamber 510 may include the chamber 301, the valve 512 may include the piston member 322, the handle 514 may include the lever member 300, the source 516 may include the canister 204, the piston 518 may include the piston 208, and the drive may include the piston 222 (e.g., as shown in FIGS. 9-12).

Figure 23:
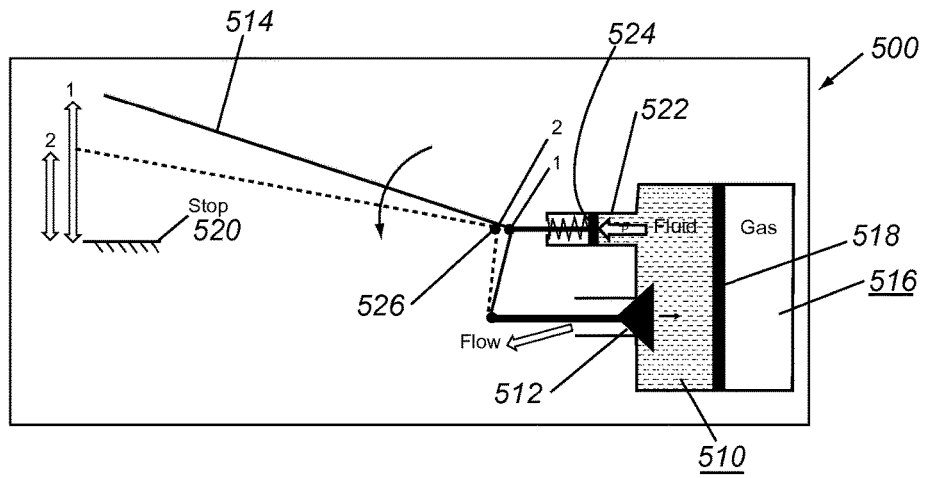
FIG. 23 is a schematic of an exemplary embodiment of an actuator for a lens inserter using pressure feedback.

In addition, in the embodiment shown in FIG. 23, an actuator 500 may also include one or more additional components to provide pressure feedback. For example, the handle 514 may include a fixed stop 520 that provides a limit to movement of the handle 514, thereby providing a maximum open position for the valve 512. In addition, a port 522 from the chamber 510 may include a secondary piston 524 slidable therein that is coupled to a movable pivot 526 of the handle 514. In this configuration, if pressure within the chamber 510 increases, the fluid pressure may be projected into the chamber 510 (represented by arrow "P"), advance the secondary piston 524 and move the handle pivot 526 outwardly (e.g., from position 1 to position 2), thereby changing the movement of the handle 514 relative to the stop 520 and reduce the maximum valve opening. Thus, as the pressure within the chamber 510 increases due to temperature increases, movement of the handle 514 may be limited.

Figure 24:
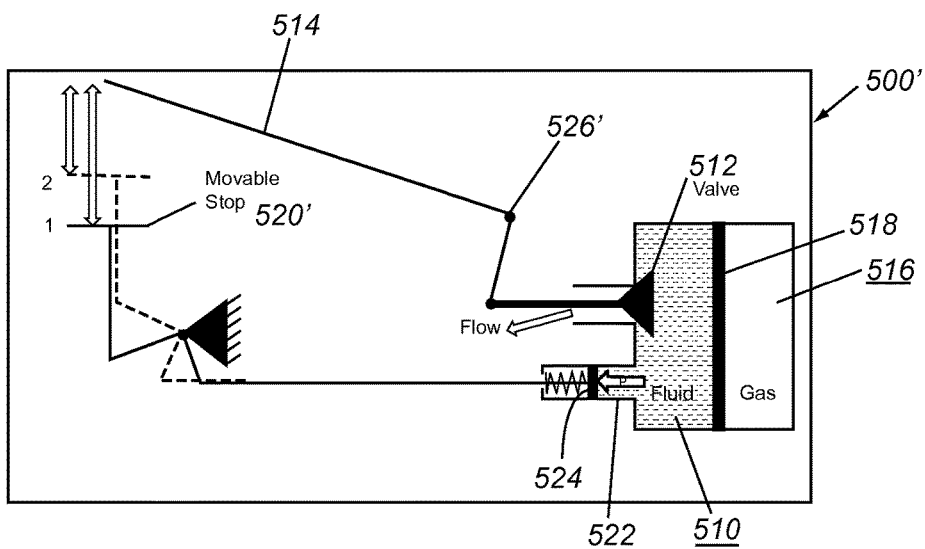
FIG. 24 is a schematic of another exemplary embodiment of an actuator for a lens inserter using pressure feedback.

Alternatively, as shown in FIG. 24, another actuator 500' is shown generally similar to the actuator 500 of FIG. 23, except that the handle pivot 524' is substantially fixed and the stop 520' is movable to provide a similar limit on movement of the handle 514. In this embodiment, the secondary piston 524 in the port 522 may be coupled to the stop 520,' to move the handle stop 520' (e.g., from position 1 to position 2) to reduce the maximum valve opening as the pressure (represented by arrow "P") increases due to temperature increases.

In these embodiments, the secondary piston 524 may be biased to an inward position such that as temperature and pressure decrease, the movement of the handle 514 may automatically return to its full range of motion.

Figure 25:
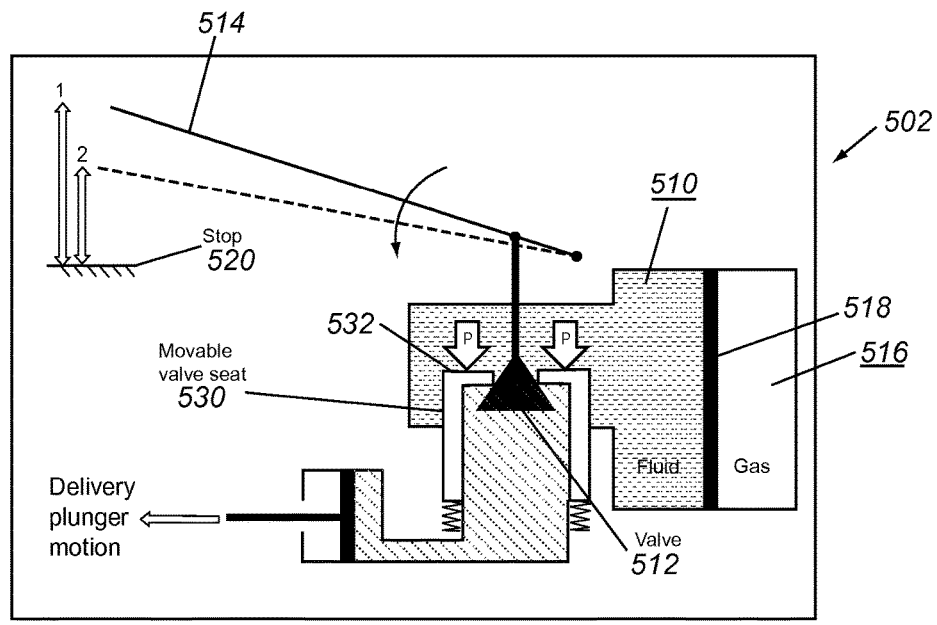
FIG. 25 is a schematic of yet another exemplary embodiment of an actuator for a lens inserter using pressure feedback.

Turning to FIG. 25, another embodiment of an actuator 502 is shown that also generally includes a chamber 510 of viscous fluid, a valve 512, a handle 514 and stop 520, a source of pressurized gas 516, and a piston 518 for pressurizing the chamber 510, similar to the previous embodiments. In addition, the actuator 502 includes a valve seat 530 movable relative to the chamber 510, e.g., including a pressure surface 532 exposed to the fluid from the chamber 510. As the pressure within the chamber 510 increases (as represented by arrows "P"), the valve seat 530 may move relative to the valve 512 to reduce the maximum valve opening. For example, as shown, as the pressure increases due to temperature, the valve seat 530 may move outwardly from the chamber 510, thereby directing the valve 512 outwardly and the handle 510 from position 1 to position 2, thereby limiting the range of motion of the handle 510 between the closed position and the maximum open position (when the handle 510 reaches the stop 520) and reducing the maximum valve opening. The valve seat 530 may be biased inwardly (e.g., by one or more springs) to a base position, e.g., corresponding to a valve closed position when the pressure is below a predetermined threshold.

Figure 26:
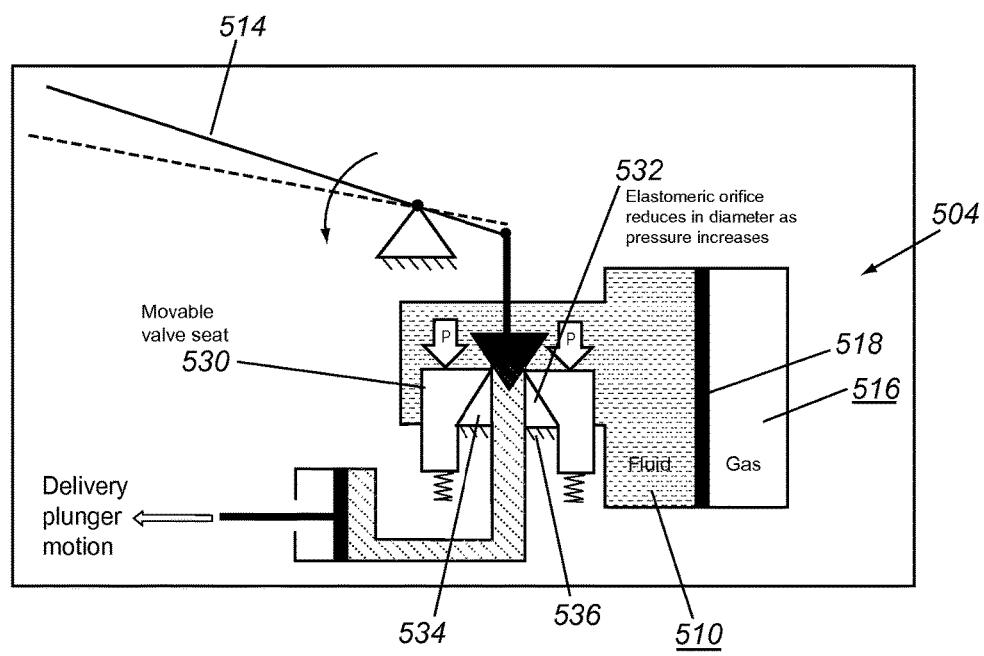
FIG. 26 is a schematic of still another exemplary embodiment of an actuator for a lens inserter using pressure feedback.

Turning to FIG. 26, another actuator 504 is shown that also includes a chamber 510 of viscous fluid, a valve 512, a handle 514 and stop 520, a source of pressurized gas 516, and a piston 518 for pressurizing the chamber 510, similar to the previous embodiments. In addition, the actuator 504 includes a valve seat 530 movable relative to the chamber 510 and an elastomeric orifice 532, e.g., defined by an annular wedge-shaped member 534 set into the valve seat 530 and/or positioned between the valve seat 530 and a fixed wall 536. Unlike the previous embodiment, the valve 512 may be configured to open into the chamber 510, e.g., away from the valve seat 530 and orifice 532 to allow fluid to flow from the chamber 510 to the drive (e.g., the piston 222 shown in FIGS. 9-12).

As pressure increases within the chamber 510 (as represented by arrows "P"), the valve seat 530 may move outwardly, compressing the orifice member 536, and thereby constricting the orifice 534 to restrict flow of fluid from the chamber 510. Thus, as the pressure increases due to temperature increases, the orifice 534 may be constricted to reduce the maximum valve opening.

Figure 27:
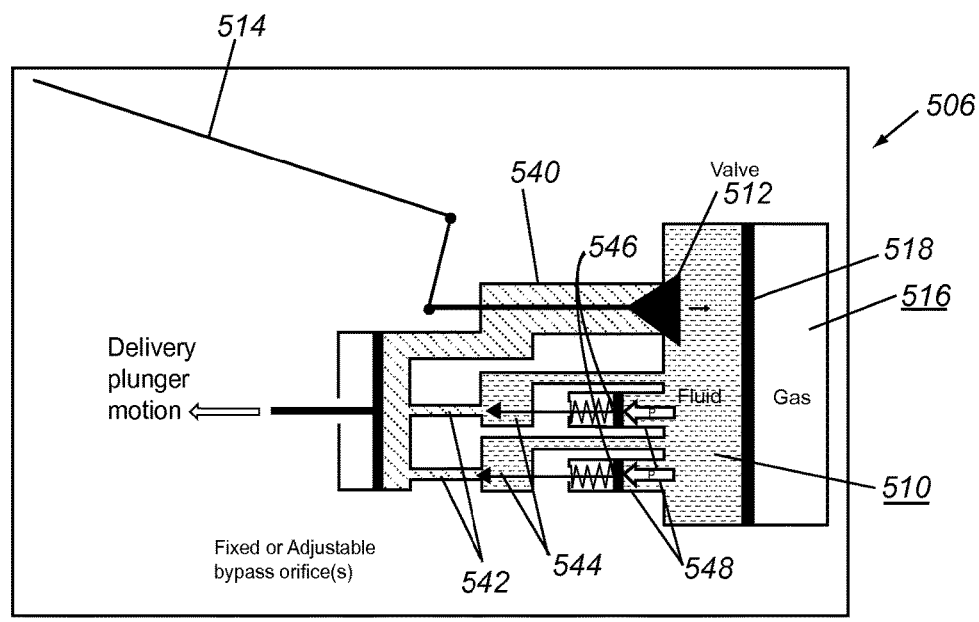
FIG. 27 is a schematic of another exemplary embodiment of an actuator for a lens inserter including bypass passages that may be restricted as temperature increases.

Turning to FIG. 27, yet another embodiment of an actuator 506 is shown that generally includes a chamber 510 of viscous fluid, a valve 512, a handle 514 and stop 520, a source of pressurized gas 516, and a piston 518 for pressurizing the chamber 510, similar to the previous embodiments. In addition to a primary fluid passage 540 selectively closed by the valve 510, one or more bypass passages 542 are provided (e.g., two as shown) that all communicate with the device drive (e.g., the piston 222 of inserter 100A). Each bypass passage 542 includes a valve 544 controlled by a secondary piston 546 movable within a port 548 communicating with the chamber 510.

As the pressure increases due to temperature increases), the pressure within the chamber 510 (represented by arrows "P") may direct each secondary piston 546 outwardly to seal an orifice of the bypass passage 542, thereby limiting flow through the bypass passage 542. Optionally, multiple bypass passages may be provided that include valves that are actuated at different temperatures (e.g., by providing different biases for the secondary pistons 546 to resist the pressure P). In this option, as the temperature and pressure increases, the valves may close the bypass passages sequentially to provide decreasing maximum fluid flow from the chamber 510 to the drive, which may provide a smoother transition across the temperature range.

Figure 28:
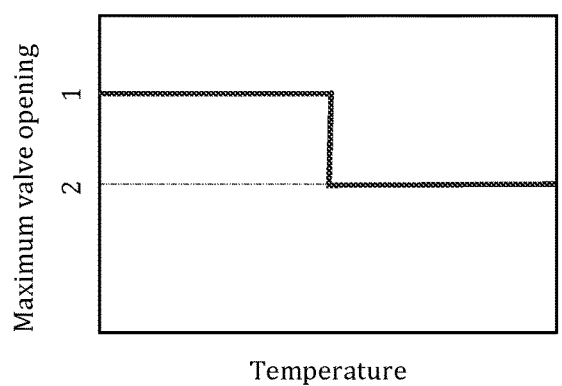
FIGS. 28-30 are graphs showing examples of using an actuator including one or more bypass passages, such as that shown in FIG. 27, to provide one or more temperature-sensitive valves that limit valve opening of an actuator.
Figure 29:
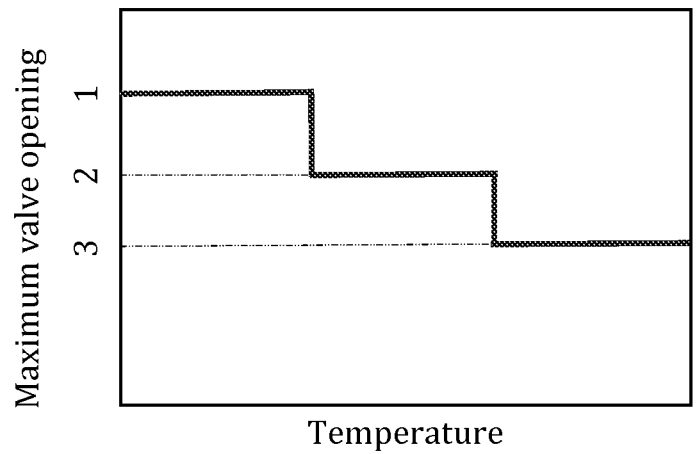
Figure 30:
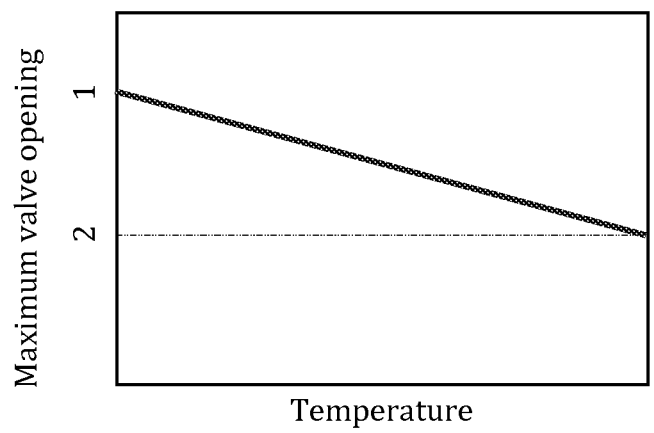

FIGS. 28-30 show various potential implementations of an actuator, such as that shown in FIG. 27 in which a primary fluid passage and one or more bypass passages are provided. For example, FIG. 28 shows how the total orifice area (and fluid flow rate) would change with a single bypass passage and bi-stable valve (not shown) that closed at or above a predetermined temperature, e.g., in the middle of an anticipated operating temperature range. As the temperature increases (i.e., to the right), the maximum valve opening decreases when the bypass valve closes the bypass passage.

FIG. 29 shows how the total orifice area could change with two bi-stable valves that each close at a separate temperature in the temperature range, e.g., similar to the actuator 506 shown in FIG. 27. As the temperature increases, the maximum valve opening decreases as each bypass valve closes, thereby progressively restricting fluid flow as each bypass passage is closed.

FIG. 30 shows an alternative embodiment of an actuator that includes a primary fluid flow passage and a single bypass passage that includes a variable valve orifice, e.g., similar to the valve configuration shown in FIG. 26 for the bypass passage. FIG. 30 shows how the maximum valve opening changes as the variable orifice valve progressively closes as the temperature increases. At a predetermined maximum temperature, the bypass valve may be set to fully close such that the maximum valve opening is defined only by the primary control valve.

Figure 31:
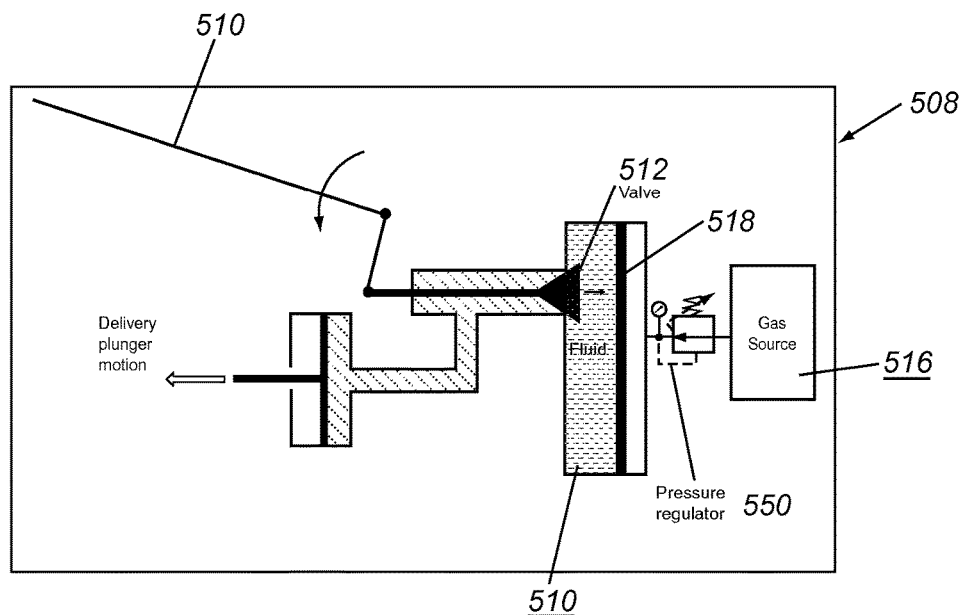
FIG. 31 is a schematic of an exemplary embodiment of an actuator for a lens inserter including a pressure regulator.

Turning to FIG. 31, another exemplary embodiment of an actuator 508 is shown that generally includes a chamber 510 of viscous fluid, a valve 512, a handle 514, a source of pressurized gas 516, and a piston 518 for pressurizing the chamber 510, similar to the previous embodiments. In addition, the actuator 508 includes a pressure regulator 550, which may be provided between the gas source 516 and the fluid divider piston 518. The pressure regulator 550 may be configured to provide a substantially constant pressure output as temperature increases.

Figure 32:
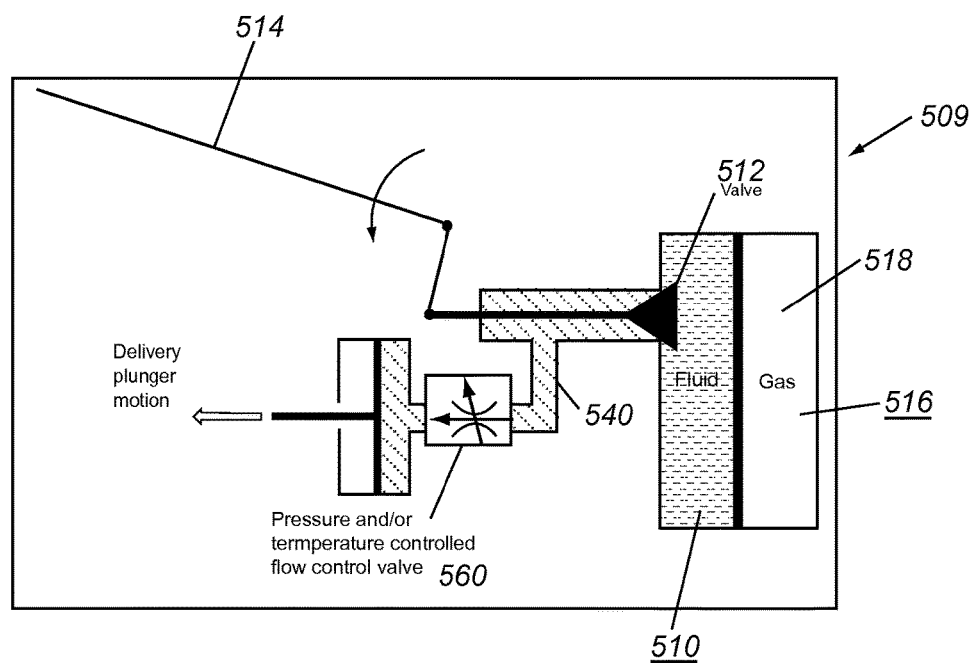
FIG. 32 is a schematic of an exemplary embodiment of an actuator for a lens inserter including a pressure and/or temperature compensated flow control valve.

FIG. 32 shows another exemplary embodiment of an actuator 509 that also includes a chamber 510 of viscous fluid, a valve 512, a handle 514, a source of pressurized gas 516, and a piston 518 for pressurizing the chamber 510, similar to the previous embodiments. In addition, the actuator 509 includes a pressure and/or temperature compensated flow control valve 560 for limiting fluid flow from the chamber 510. As shown, the flow control valve 560 may be provided in the primary flow path 540 between the primary flow valve 512 and the delivery plunger piston or other drive, and may be configured to provide a substantially stable maximum flow rate independent of the temperature or gas pressure.

In the embodiments shown in FIGS. 31 and 32, the device (e.g., the inserter 100) may include one or more sensors, e.g., a temperature sensor that provides ambient temperature data. A processor or other controller coupled to the pressure controller 550 and/or flow control valve 560 use the data to operate the system to compensate for increases in temperature.

While these embodiments are shown to use fluid pressure resulting from the changing vapor pressure of the liquefied gas as the primary feedback and actuation feature, alternatively, similar actuators and methods could also be accomplished using sensing and actuating devices that provide movement or force that varies with temperature. There are many common forms of these devices that include but not limited to:

- Thermal expansion of a solid or liquid, such as bimetallic strips, mercury thermometer where the change in temperature creates a change in length or volume that can be used as an actuator.
- Thermal expansion of a gas that can be used to drive an actuator such as a bourdon tube.
- Thermoelectric potential such as thermocouples that can be used to provide input to electrical devices that can move actuators to provide the same methods to control maximum valve opening.
- Electrical resistance changes with temperature such as thermistors that can be used to provide input to electrical devices that can move actuators to provide the same methods to control maximum valve opening.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An intraocular lens inserter comprising:
   an intraocular lens portion configured to receive an intraocular lens for insertion into an eye of an animal; and
   an actuator portion comprising a plunger configured to deliver an intraocular lens from the intraocular lens portion, a source of pressurized fluid, a valve, an actuator coupled to the valve configured to selectively open a flow path from the source to the plunger to control flow of the pressurized fluid to advance the plunger to deliver the intraocular lens at a desired rate, and a pressure feedback device configured to limit movement of the actuator to reduce a maximum valve opening position of the valve as temperature rises.

2. The intraocular lens inserter of claim 1, wherein the pressure feedback device comprises a port communicating with the source of pressurized fluid, and a piston movable within the port and coupled to the actuator to limit movement of the actuator based on pressure within the source of pressurized fluid.

3. The intraocular lens inserter of claim 2, wherein the piston is coupled to the actuator to move a pivot of the actuator and thereby reduce range of motion of the actuator and thereby reduce the maximum valve opening position of the valve as pressure within the source of pressurized fluid increases as the temperature rises.

4. The intraocular lens inserter of claim 2, further comprising an actuator stop configured to limit movement of the actuator from a valve closed to position to a maximum open position, and wherein the piston is coupled to the actuator stop to move the actuator stop and thereby reduce range of motion of the actuator and thereby reduce the maximum valve opening position of the valve as pressure within the source of pressurized fluid increases as the temperature rises.

5. The intraocular lens inserter of claim 1, further comprising an energy storage device configured to provide pressure to the source of pressurized fluid.

6. The intraocular lens inserter of claim 5, wherein the source of pressurized fluid comprises a chamber including incompressible fluid, and wherein the energy storage device comprises a piston communicating with the chamber and biased to apply a predetermined pressure to the chamber via the piston.

7. The intraocular lens inserter of claim 6, wherein the energy source comprises one of a canister of pressurized gas and a spring configured to bias the piston.

8. The intraocular lens inserter of claim 5, wherein the source of pressurized fluid comprises a chamber including viscous fluid, and wherein the energy storage device comprises a canister of pressurized compressible fluid and a piston communicating with the chamber such that compressible gas from the canister applies a predetermined pressure to the chamber via the piston.

9. The intraocular lens inserted of claim 1, wherein the source of pressurized fluid comprises a chamber within the actuator portion that includes an incompressible, viscous fluid.

10. An intraocular lens inserter comprising:
    an intraocular lens portion configured to receive an intraocular lens for insertion into an eye of an animal; and
    an actuator portion comprising:
      a plunger configured to deliver an intraocular lens from the intraocular lens portion;
      a source of pressurized fluid;
      a primary flow path from the source of pressurized fluid to the plunger;
      an actuator coupled to a valve configured to selectively open the primary flow path to control flow of the pressurized fluid to advance the plunger and deliver the intraocular lens at a desired rate;
      a bypass flow path from the source of pressurized fluid to the plunger; and
      a bypass valve configured to selectively close the bypass flow path based on pressure feedback from the source of pressurized fluid.

11. The intraocular lens inserter of claim 10, wherein the bypass valve is configured to close the bypass flow path when the pressure exceeds a first predetermined threshold.

12. The intraocular lens inserter of claim 11, further comprising:
    a second bypass flow path from the source of pressurized fluid to the plunger; and
    a second bypass valve configured to selectively close the second bypass flow based on pressure feedback from the source of pressurized fluid.

13. The intraocular lens inserter of claim 12, wherein the second bypass valve is configured to close the second bypass flow path when the pressure exceeds a second predetermined threshold different than the first predetermined threshold.

14. The intraocular lens inserter of claim 10, wherein the bypass valve is configured to gradually close the bypass flow path as pressure within the source of pressurized fluid increases.

* * * * *